United States Patent
Tsukada et al.

(10) Patent No.: US 11,229,355 B2
(45) Date of Patent: Jan. 25, 2022

(54) METHOD OF OPTICAL COHERENCE TOMOGRAPHY (OCT) IMAGING, METHOD OF PROCESSING OCT DATA, AND OCT APPARATUS

(71) Applicant: TOPCON CORPORATION, Tokyo (JP)

(72) Inventors: Hisashi Tsukada, Hachioji (JP); Atsushi Kubota, Itabashi-ku (JP); Yasufumi Fukuma, Wako (JP)

(73) Assignee: TOPCON CORPORATION, Tokyo (JP)

( * ) Notice: Subject to any disclaimer, the term of this patent is extended or adjusted under 35 U.S.C. 154(b) by 0 days.

(21) Appl. No.: 16/917,922

(22) Filed: Jul. 1, 2020

(65) Prior Publication Data
US 2021/0003383 A1    Jan. 7, 2021

(30) Foreign Application Priority Data

| Jul. 2, 2019 | (JP) | ............................ JP2019-123431 |
| Jul. 2, 2019 | (JP) | ............................ JP2019-123437 |
| Jul. 11, 2019 | (JP) | ............................ JP2019-129315 |

(51) Int. Cl.
*G01B 9/02* (2006.01)
*A61B 3/10* (2006.01)
(Continued)

(52) U.S. Cl.
CPC ............ *A61B 3/102* (2013.01); *A61B 3/0025* (2013.01); *A61B 3/12* (2013.01); *A61B 5/0066* (2013.01);
(Continued)

(58) Field of Classification Search
CPC ......... A61B 3/102; A61B 3/0025; A61B 3/12; A61B 5/0066; G06T 7/32; G06T 3/0068;
(Continued)

(56) References Cited

U.S. PATENT DOCUMENTS

| 7,884,945 B2 | 2/2011 | Srinivasan et al. |
| 8,405,834 B2 | 3/2013 | Srinivasan et al. |

(Continued)

FOREIGN PATENT DOCUMENTS

| JP | 6230023 B2 | 11/2017 |
| JP | 6276943 B2 | 2/2018 |

OTHER PUBLICATIONS

Partial European search report dated Nov. 24, 2020, in corresponding European patent Application No. 20182150.1, 13 pages.
(Continued)

*Primary Examiner* — Tarifur R Chowdhury
*Assistant Examiner* — Jonathon Cook
(74) *Attorney, Agent, or Firm* — Xsensus LLP

(57) ABSTRACT

An OCT imaging method of some exemplary aspects includes acquiring a first three dimensional data set by applying an OCT scan targeting a first three dimensional region of a sample, creating a first two dimensional map based on representative intensity values respectively of a plurality of pieces of A-scan data included in the first three dimensional data set, designating a second three dimensional region of the sample based on the first two dimensional map, acquiring a second three dimensional data set by applying an OCT scan targeting the second three dimensional region, and generating image data from at least part of the second three dimensional data set.

19 Claims, 11 Drawing Sheets

(51) Int. Cl.
  *A61B 5/00*    (2006.01)
  *G06T 7/32*    (2017.01)
  *A61B 3/00*    (2006.01)
  *A61B 3/12*    (2006.01)
  *G06T 3/00*    (2006.01)
  *G06T 3/20*    (2006.01)
  *G06T 3/60*    (2006.01)

(52) U.S. Cl.
  CPC ..... *G01B 9/02083* (2013.01); *G01B 9/02091* (2013.01); *G06T 3/0068* (2013.01); *G06T 3/20* (2013.01); *G06T 3/60* (2013.01); *G06T 7/32* (2017.01); *G06T 2200/04* (2013.01); *G06T 2207/10101* (2013.01); *G06T 2207/20212* (2013.01); *G06T 2207/30041* (2013.01)

(58) Field of Classification Search
  CPC ......... G06T 3/20; G06T 3/60; G06T 2200/04; G06T 2207/10101; G06T 2207/30041; G06T 2207/20212; G01B 9/02083; G01B 9/02091
  See application file for complete search history.

(56) References Cited

U.S. PATENT DOCUMENTS

| | | |
|---|---|---|
| 2007/0070295 A1 | 3/2007 | Tsukada et al. |
| 2007/0216909 A1 | 9/2007 | Everett et al. |
| 2010/0208201 A1 | 8/2010 | Knighton et al. |
| 2011/0134394 A1 | 6/2011 | Srinivasan et al. |
| 2013/0003077 A1* | 1/2013 | Suehira .............. G01B 9/02087 356/479 |
| 2013/0301001 A1 | 11/2013 | Carnevale |
| 2014/0293289 A1 | 10/2014 | Reisman |
| 2015/0042952 A1* | 2/2015 | Uchida ................. G06T 7/11 351/206 |
| 2016/0198940 A1 | 7/2016 | Shibutani et al. |
| 2017/0209037 A1* | 7/2017 | Sumiya ................ A61B 3/1025 |
| 2018/0003479 A1* | 1/2018 | Tomatsu ............ G01B 9/02087 |
| 2019/0000313 A1 | 1/2019 | Sadda et al. |
| 2019/0150729 A1 | 5/2019 | Huang et al. |

OTHER PUBLICATIONS

Partial European search report dated Dec. 2, 2020, in corresponding European patent Application No. 20182152.7, 11 pages.

Zhang et al., "Adaptive Optics with Combined Optical Coherence Tomography and Scanning Laser Ophthalmoscopy for in vivo mouse retina imaging", Proc. of SPIE, vol. 10474, Feb. 22, 2018, pp. 1047427-1-1047427-9, total 9 pages, XP060100531.

Pohit and J Sharma M: "Image registration under translation and rotation in two-dimensional planes using Fourier slice theorem", Applied Optics, Optical Society of America, Washington, DC, US, vol. 54, No. 14, May 10, 2015 (May 10, 2015), pp. 4514-4519, XP001595215.

Uji Akihito et al: "Impact of Multiple En Face Image Averaging on Quantitative Assessment from Optical Coherence Tomography Angiography Images", Ophthalmology, vol. 124, No. 7, Mar. 17, 2017 (Mar. 17, 2017), pp. 944-952, XP085094408.

Extended European Search Report dated Mar. 5, 2021 in European Application No. 20182150.1.

Extended European search report dated Nov. 20, 2020, in corresponding European patent Application No. 20182149.3, 9 pages.

Shuliang Jiao et al., "Simultaneous acquisition of sectional and fundus ophthalmic images with spectral-domain optical coherence tomography", Optics Express, Jan. 24, 2005, pp. 444-452, vol. 13, No. 2, 2005 optical Society of America, US.

U.S. Office Action dated Jun. 24, 2021 in U.S. Appl. No. 16/916,154, 39 pages.

* cited by examiner

300

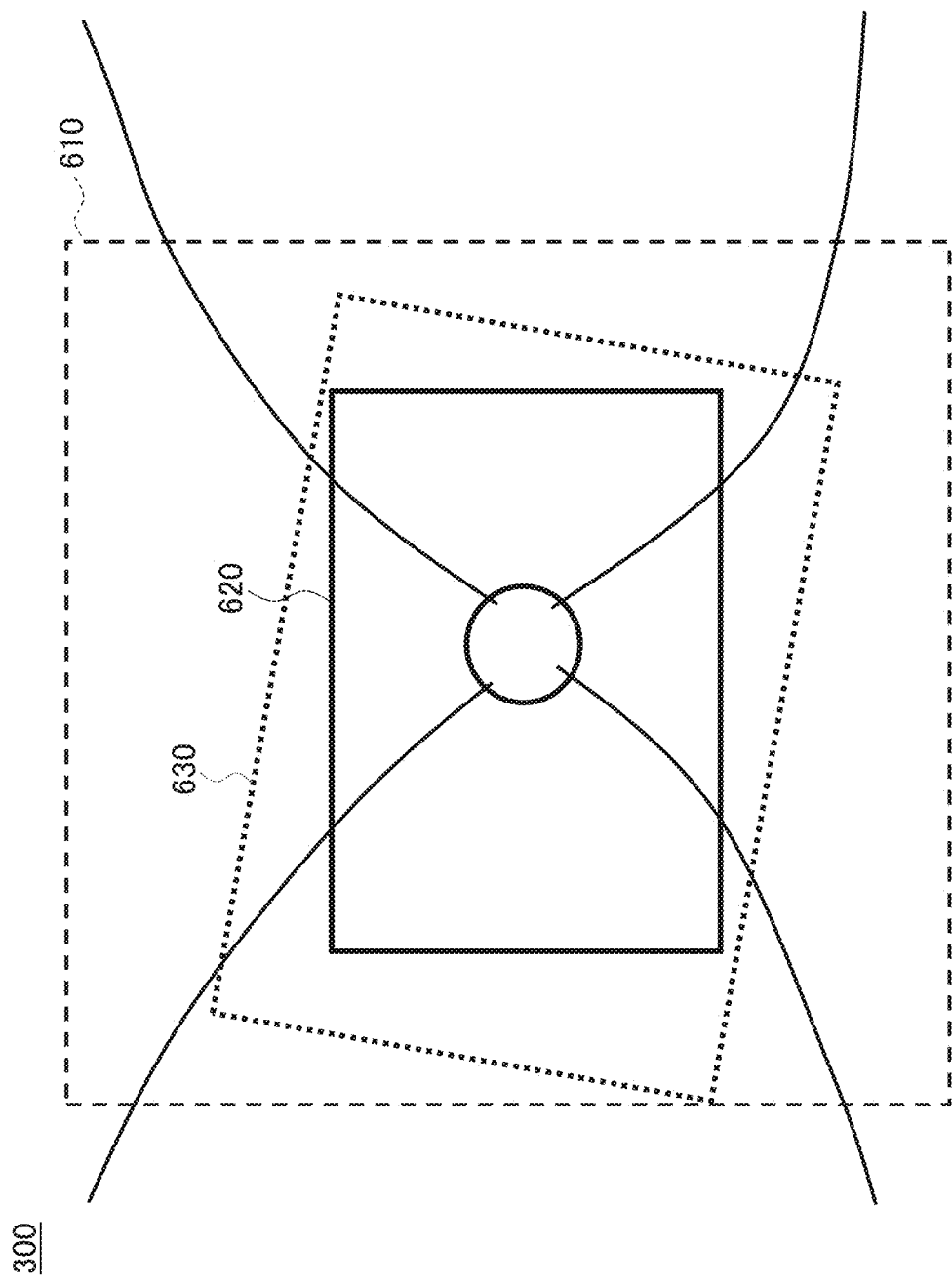

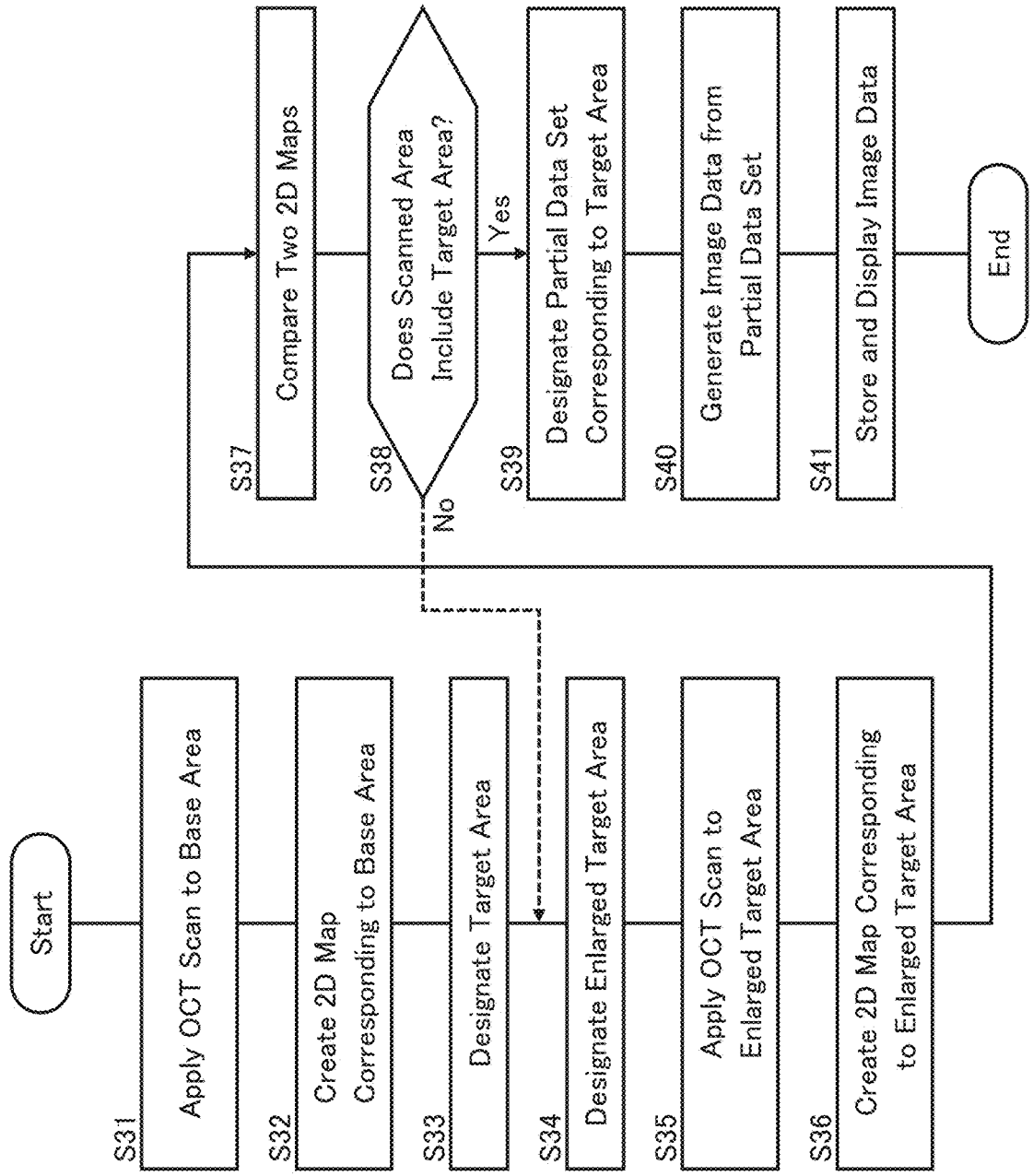

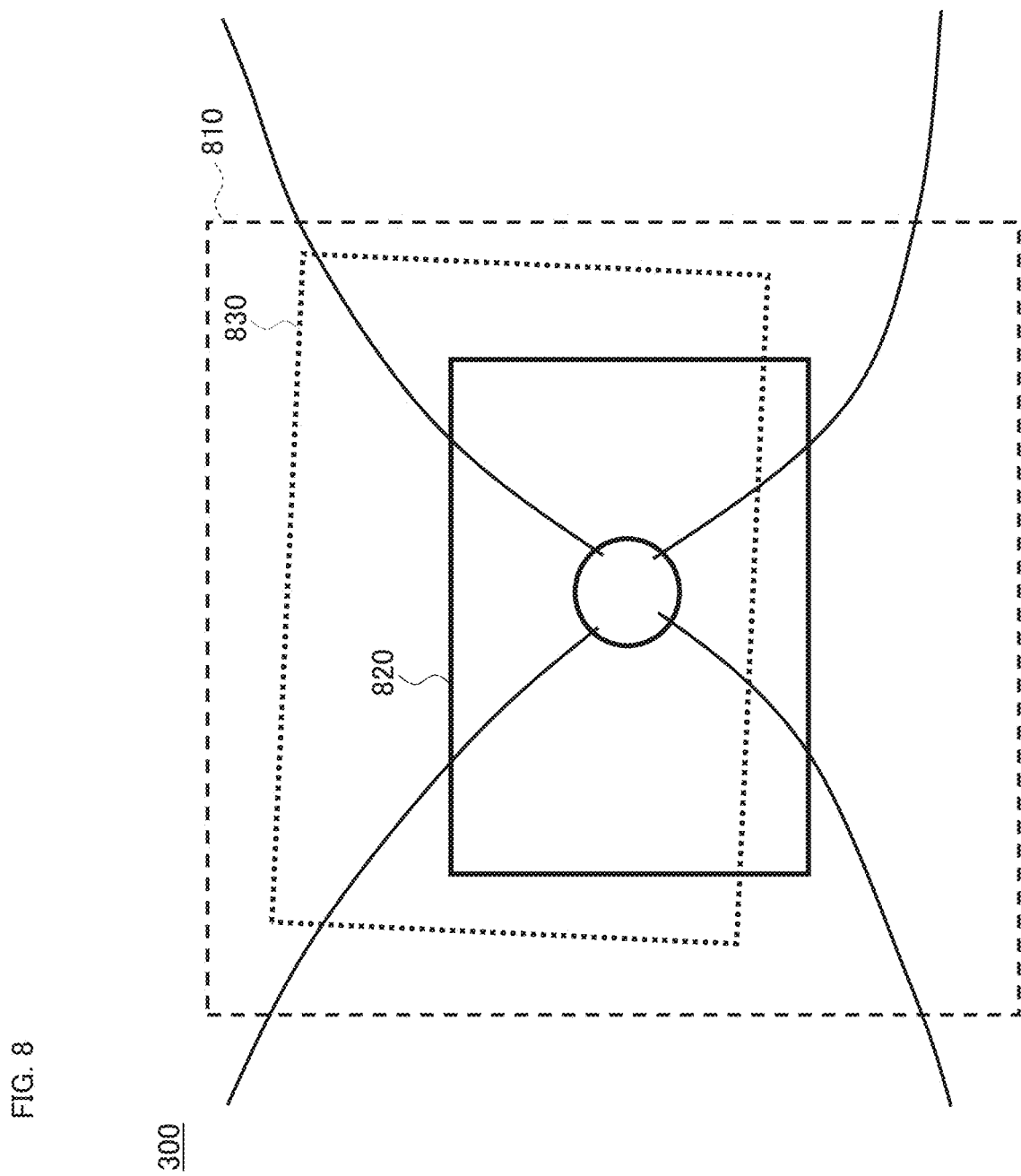

METHOD OF OPTICAL COHERENCE TOMOGRAPHY (OCT) IMAGING, METHOD OF PROCESSING OCT DATA, AND OCT APPARATUS

CROSS-REFERENCE TO RELATED APPLICATIONS

This application is based upon and claims the benefit of priority from Japanese Patent Applications No. 2019-123431, filed Jul. 2, 2019, No. 2019-123437, filed Jul. 2, 2019, and No. 2019-129315, filed Jul. 11, 2019; the entire contents of each are incorporated herein by reference.

FIELD

The present disclosure relates generally to a method of OCT imaging, a method of processing OCT data, and an OCT apparatus.

BACKGROUND

OCT is an imaging technique capable of representing a light scattering medium at a resolution of micrometer level or less, and is used for medical imaging, nondestructive testing and the like. OCT is a low-coherence-interferometry-based technique and typically utilizes near infrared light to ensure the reaching depth of the light into a sample of a scattering medium.

U.S. Pat. No. 7,884,945 discloses a method of processing an OCT data set represented as a function of optical depths that is obtained by a measurement of backscattering or back reflection in order to acquire OCT data efficiently and to acquire OCT data from a specific region of a sample accurately and in a short time. The method includes a step of analyzing an OCT data set to identify landmark region data of at least the first subset, a step of placing the OCT data set based on the landmark region data, and a step of processing at least the second subset of the OCT data set based on the correspondence between the OCT data set and the landmark region data.

Further, U.S. Pat. No. 8,405,834 discloses a method for monitoring disease progression. The method includes a step of acquiring an OCT survey scan data set represented as a function of optical depths that is obtained by a measurement of backscattering or back reflection, a step of analyzing the survey scan data set to identify a landmark region, a step of assigning a location in the sample or a location relating to a fixed position to an element of the survey scan data set to register part of the survey scan data set representing at least part of a diseased or affected tissue region relating to the landmark region, and a step of monitoring the changes in the diseased or affected tissue region at different points in time.

SUMMARY

An object of the present disclosure is to make further improvements on the efficiency of OCT scanning or OCT data processing.

Some exemplary aspects are a method of imaging using optical coherence tomography (OCT), including: acquiring a first three dimensional data set by applying an OCT scan targeting a first three dimensional region of a sample; creating a first two dimensional map based on representative intensity values respectively of a plurality of pieces of A-scan data included in the first three dimensional data set; designating a second three dimensional region of the sample based on the first two dimensional map; acquiring a second three dimensional data set by applying an OCT scan targeting the second three dimensional region; and generating image data from at least part of the second three dimensional data set.

Any of the following optional aspects may be combined with an OCT imaging method of some exemplary aspects: designating the second three dimensional region includes: based on the first two dimensional map, designating a target region that is a three dimensional region included in the first three dimensional region; and designating the second three dimensional region to include the target region; designating the second three dimensional region to include the target region and be included in the first three dimensional region; creating a second two dimensional map based on representative intensity values respectively of a plurality of pieces of A-scan data included in the second three dimensional data set, designating a partial data set of the second three dimensional data set by a comparison between the first two dimensional map and the second two dimensional map, and generating the image data from the partial data set; the comparison includes an image correlation calculation; determining a positional difference amount between the first two dimensional map and the second two dimensional map by the comparison; the positional difference amount includes at least one of a translation amount and a rotation amount; designating the second three dimensional region includes, based on the first two dimensional map, designating a target region that is a three dimensional region included in the first three dimensional region and designating the second three dimensional region to include the target region and be included in the first three dimensional region, and designating the partial data set by designating part of the second three dimensional data set corresponding to the target region based on a result of the comparison; determining whether or not the second three dimensional data set includes a target data set corresponding to the target region based on the result of the comparison; designating the target data set as the partial data set in the event that the second three dimensional data set is determined to include the target data set; acquiring another second three dimensional data set by applying another OCT scan targeting the second three dimensional region of the sample in the event that the second three dimensional data is determined not to include the target data set, and generating image data from at least part of the another second three dimensional data set; designating another second three dimensional region of the sample in the event that the second three dimensional data set is determined not to include the target data set, wherein acquiring the another second three dimensional data set by applying an OCT scan targeting the another second three dimensional region; designating the another second three dimensional region includes designating another target region that is a three dimensional region included in the first three dimensional region, and designating the another second three dimensional region to include the another target region; designating the another second three dimensional region to include the another target region and be included in the first three dimensional region; designating the another second three dimensional region based on the result of the comparison; designating the another second three dimensional region by changing a position of the second three dimensional region based on the result of the comparison; a size of the another second three dimensional region is larger than a size of the second three dimensional region.

Some exemplary aspects are a method of processing data acquired using optical coherence tomography (OCT), including: receiving a first three dimensional data set acquired by an OCT scan targeting a first three dimensional region of a sample; creating a first two dimensional map based on representative intensity values respectively of a plurality of pieces of A-scan data included in the first three dimensional data set; designating a second three dimensional region of the sample based on the first two dimensional map; receiving a second three dimensional data set acquired by an OCT scan targeting the second three dimensional region; and generating image data from at least part of the second three dimensional data set.

Some exemplary aspects are an optical coherence tomography (OCT) apparatus including: an OCT scanner that applies an OCT scan to a sample; a first controlling unit that controls the OCT scanner to acquire a first three dimensional data set by applying an OCT scan targeting a first three dimensional region of a sample; a map creating unit that creates a first two dimensional map based on representative intensity values respectively of a plurality of pieces of A-scan data included in the first three dimensional data set; a region designating unit that designates a second three dimensional region of the sample based on the first two dimensional map; a second controlling unit that controls the OCT scanner to acquire a second three dimensional data set by applying an OCT scan targeting the second three dimensional region; and an image data generating unit that generates image data from at least part of the second three dimensional data set.

Any of the following optional aspects may be combined with an OCT apparatus of some exemplary aspects: the region designating unit designates a target region that is a three dimensional region included in the first three dimensional region, and designates the second three dimensional region to include the target region, based on the first two dimensional map; the region designating unit designates the second three dimensional region to include the target region and be included in the first three dimensional region; the map creating unit creates a second two dimensional map based on representative intensity values respectively of a plurality of pieces of A-scan data included in the second three dimensional data set, and the image data generating unit designates a partial data set of the second three dimensional data set by a comparison between the first two dimensional map and the second two dimensional map, and generates the image data from the partial data set; the comparison includes an image correlation calculation; the image data generating unit determines a positional difference amount between the first two dimensional map and the second two dimensional map by the comparison; the positional difference amount includes at least one of a translation amount and a rotation amount; based on the first two dimensional map, the region designating unit designates a target region that is a three dimensional region included in the first three dimensional region, and designates the second three dimensional region to include the target region and be included in the first three dimensional region, and the image data generating unit designates part of the second three dimensional data set corresponding to the target region as the partial data set based on a result of the comparison; the image data generating unit determines whether or not the second three dimensional data set includes a target data set corresponding to the target region based on the result of the comparison; the image data generating unit designates the target data set as the partial data set in the event that the second three dimensional data set is determined to include the target data set; the second controlling unit controls the OCT scanner to acquire another second three dimensional data set by applying another OCT scan targeting the second three dimensional region of the sample in the event that the second three dimensional data set is determined not to include the target data set, and the image data generating unit generates image data from at least part of the another second three dimensional data set; the region designating unit designates another second three dimensional region of the sample in the event that the second three dimensional data set is determined not to include the target data set, and the second controlling unit controls the OCT scanner to acquire the another second three dimensional data set by applying an OCT scan targeting the another second three dimensional region; the region designating unit designates another target region that is a three dimensional region included in the first three dimensional region, and designates the another second three dimensional region to include the another target region, in the event that the second three dimensional data set is determined not to include the target data set; the region designating unit designates the another second three dimensional region to include the another target region and be included in the first three dimensional region; the region designating unit designates the another second three dimensional region based on the result of the comparison; the region designating unit designates the another second three dimensional region by changing a position of the second three dimensional region based on the result of the comparison; a size of the another second three dimensional region is larger than a size of the second three dimensional region.

Some exemplary aspects are a method of controlling an OCT apparatus that includes a processor and an optical coherence tomography (OCT) scanner configured to apply an OCT scan to a sample, the method including: controlling the OCT scanner to acquire a first three dimensional data set by applying an OCT scan targeting a first three dimensional region of a sample; controlling the processor to create a first two dimensional map based on representative intensity values respectively of a plurality of pieces of A-scan data included in the first three dimensional data set; controlling the processor to designate a second three dimensional region of the sample based on the first two dimensional map; controlling the OCT scanner to acquire a second three dimensional data set by applying an OCT scan targeting the second three dimensional region; and controlling the processor to generate image data from at least part of the second three dimensional data set.

Some exemplary aspects are an optical coherence tomography (OCT) data processing apparatus that processes data acquired by using OCT, the apparatus comprising: a first receiving unit that receives a first three dimensional data set acquired by an OCT scan targeting a first three dimensional region of a sample; a map creating unit that creates a first two dimensional map based on representative intensity values respectively of a plurality of pieces of A-scan data included in the first three dimensional data set; a region designating unit that designates a second three dimensional region of the sample based on the first two dimensional map; a second receiving unit that receives a second three dimensional data set acquired by an OCT scan targeting the second three dimensional region; and an image data generating unit that generates image data from at least part of the second three dimensional data set.

Some exemplary aspects are a method of controlling an optical coherence tomography (OCT) data processing apparatus including a processor, the method comprising: controlling the processor to receive a first three dimensional data set acquired by an OCT scan targeting a first three dimensional region of a sample; controlling the processor to create a first two dimensional map based on representative intensity values respectively of a plurality of pieces of A-scan data included in the first three dimensional data set; controlling the processor to designate a second three dimensional region of the sample based on the first two dimensional map; controlling the processor to receive a second three dimensional data set acquired by an OCT scan targeting the second three dimensional region; and controlling the processor to generate image data from at least part of the second three dimensional data set.

Some exemplary aspects are a program that causes a computer to execute the method of any one of the aspects.

Some exemplary aspects are a computer-readable non-transitory recording medium storing the program of any one of the aspects.

According to some exemplary aspects, improvements on the efficiency of OCT scanning or OCT data processing may be achieved.

BRIEF DESCRIPTION OF THE DRAWINGS

FIG. 6 is a schematic diagram for describing processing performed by the ophthalmic apparatus according to the exemplary aspect.

FIG. 7 is a flowchart illustrating the operation of the ophthalmic apparatus according to the exemplary aspect.

FIG. 8 is a schematic diagram for describing processing performed by the ophthalmic apparatus according to the exemplary aspect.

DETAILED DESCRIPTION

Figure 1:
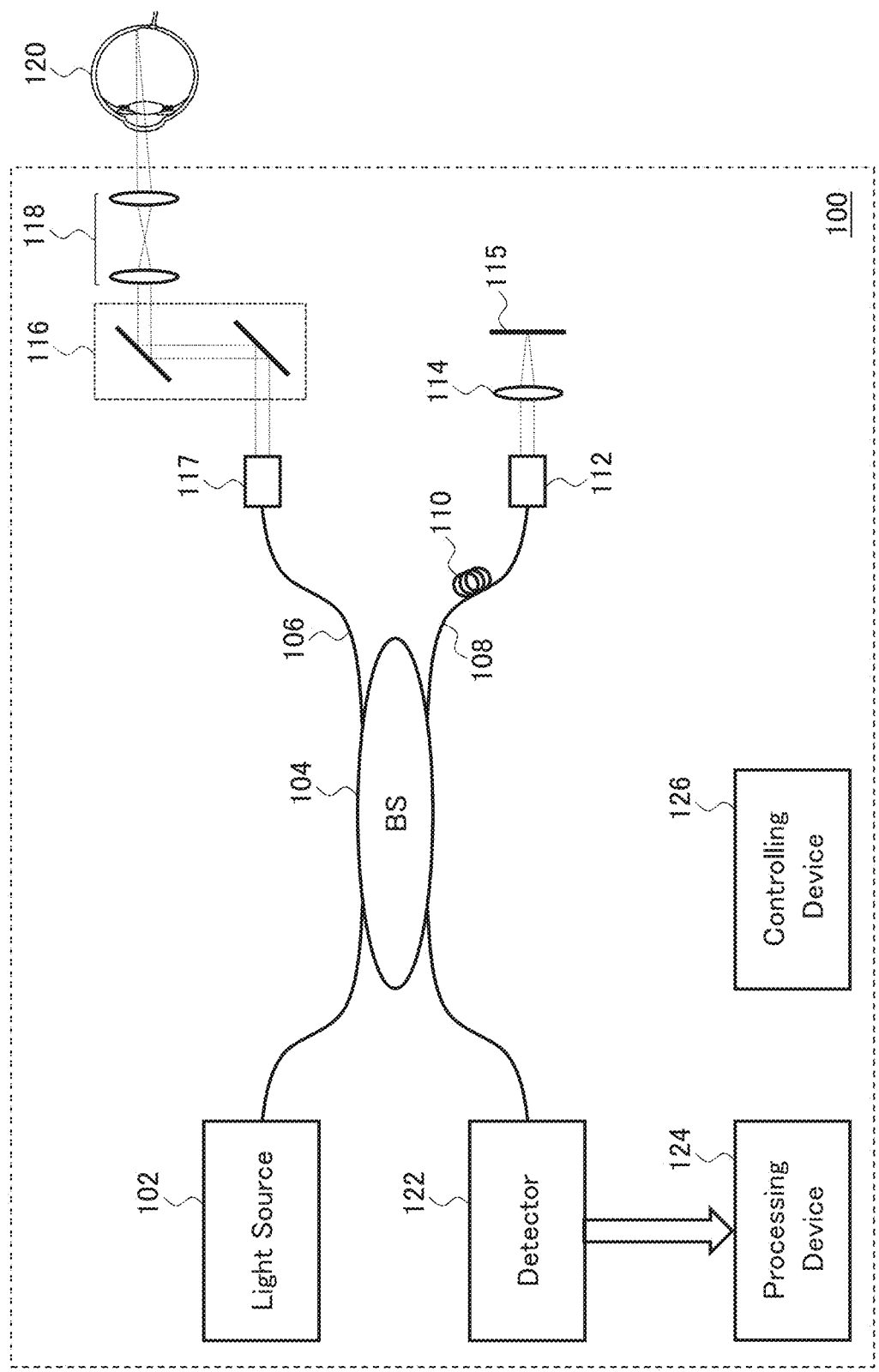
FIG. 1 is a schematic diagram illustrating the configuration of the ophthalmic apparatus (OCT apparatus) according to the exemplary aspect.

Some exemplary aspects of embodiments are described below. Note that any of the items disclosed in the documents cited in the present specification may be incorporated into the exemplary aspects. Also, any items relating to known technologies or known techniques may be incorporated into the exemplary aspects.

Some exemplary aspects relate to techniques for processing a three dimensional data set acquired by applying an OCT scan to a three dimensional region of a sample. Some exemplary aspects are applicable to various types of processing such as setting of a region on which an OCT scan is performed, registration between OCT images, analysis, measurement and segmentation of OCT images, thereby contributing to improvements on the efficiency of OCT scanning and/or OCT data processing.

In some exemplary aspects, a "processor" is, for example, a circuit (circuitry) such as a central processing unit (CPU), a graphics processing unit (GPU), an application specific integrated circuit (ASIC), a programmable logic device (e.g., a simple programmable logic device (SPLD)), a complex programmable logic device (CPLD), a field programmable gate array (FPGA), or the like. The processor provides some examples for realizing desired functions, for example, by reading out and executing a program stored in a storage circuit or a storage device.

The type of OCT applicable to some exemplary aspects is optional, and is typically swept source OCT or spectral domain OCT. However, other types of OCT may be employed.

Swept source OCT is an imaging technique performed by splitting light emitted from a wavelength tunable light source into measurement light and reference light, superposing the return light of the measurement light returned from the sample with the reference light to generate interference light, detecting the interference light with a photodetector, and applying Fourier transform and other processes to the detected data acquired according to the wavelength sweeping and the measurement light scanning.

Spectral domain OCT is an imaging technique performed by splitting light emitted from a low coherence light source (broadband light source) into measurement light and reference light, superposing the return light of the measurement light returned from the sample with the reference light to generate interference light, detecting the interference light using a spectrometer to obtain the spectral distribution thereof, and applying Fourier transform and other processes to the spectral distribution detected.

In brief, swept source OCT is an OCT technique of acquiring the spectral distribution of the interference light by time division, and spectral domain OCT is an OCT technique of acquiring the spectral distribution of the interference light by space division.

Types other than such Fourier domain OCT include time domain OCT and en-face OCT (or full field OCT). Time domain OCT introduces mechanical and sequential scanning in the axial direction (Z direction). En-face OCT provides two dimensional imaging of the XY plane orthogonal to the Z direction.

The exemplary aspects described below may be used in ophthalmic imaging, analysis, measurement, evaluation and the like. However, some exemplary aspects may be used in any fields other than ophthalmology such as medical departments other than ophthalmology (e.g., dermatology, dentistry, surgery) and industrial fields (e.g., nondestructive testing).

Figure 2:
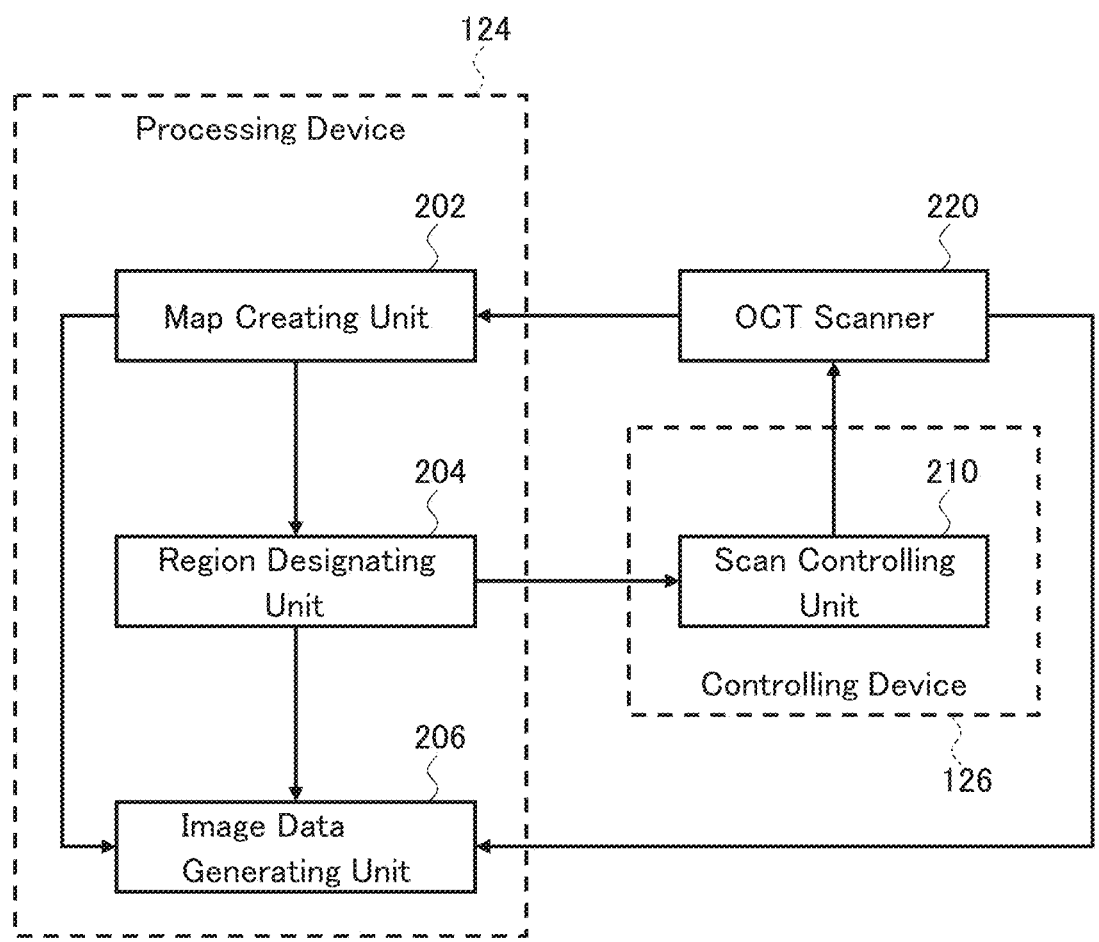
FIG. 2 is a schematic diagram illustrating the configuration of the ophthalmic apparatus according to the exemplary aspect.

FIG. 1 and FIG. 2 show the configuration of the OCT apparatus (ophthalmic apparatus) 100 according to an exemplary aspect. The ophthalmic apparatus 100 provides an OCT imaging method.

More specifically, the ophthalmic apparatus 100 is configured to acquire the first three dimensional data set by applying an OCT scan targeting the first three dimensional region of the sample (eye). Here, the first three dimensional region is set to a sufficiently wide area in some typical cases. For example, the first three dimensional region is set to the maximum scan area of the ophthalmic apparatus 100. Further, in consideration of eye movement etc., the region to which the OCT scan targeting the first three dimensional region is actually applied does not have to coincide with the first three dimensional region. However, employment of fixation, tracking, etc. allows OCT scanning to be applied to a region that almost coincides with the first three dimensional region.

In addition, the ophthalmic apparatus 100 is configured to create the first two dimensional map, based on representative intensity values respectively of a plurality of pieces of A-scan data included in the first three dimensional data set. Here, the first three dimensional data set is data on which an imaging process (e.g., Fourier transform) has not been performed. The first three dimensional data set typically consists of a plurality of pieces of A-scan data arranged in a two dimensional manner on the XY plane. Each piece of A-scan data is a spectral intensity distribution (e.g., distribution data representing the relationship between wave numbers and intensities). Note that application of Fourier transform etc. to the A-scan data yields A-scan image data representing a reflection intensity distribution (backscattering intensity distribution) along the Z direction. The processing of creating a two dimensional map from the three dimensional data set may include, for example, the processes disclosed in Japanese Patent No. 6,230,023 (US Patent Application Publication No. 2014/0293289).

Further, the ophthalmic apparatus 100 is configured to designate the second three dimensional region of the sample, based on the first two dimensional map. The data used for the designation of the second three dimensional region may be the first three dimensional region, the first three dimensional data set, the first two dimensional map, or data generated from any of the three, or a combination of any two or all of the three. Furthermore, the size of the second three dimensional region may be the same as or different from that of the first three dimensional region. In the event where the sizes are different, the size of the second three dimensional region is typically set larger than that of the first three dimensional region. In addition, the orientation of the second three dimensional region may be the same as or different from that of the first three dimensional region. Furthermore, the shape of the second three dimensional region may be the same as or different from that of the first three dimensional region.

Moreover, the ophthalmic apparatus 100 is configured to apply an OCT scan targeting the second three dimensional region to acquire the second three dimensional data set, and generate image data from at least part of the second three dimensional data set acquired. As in the case of the OCT scan targeting the first three dimensional region, the region to which the OCT scan targeting the second three dimensional region is actually applied does not have to coincide with the second three dimensional region. However, employment of fixation, tracking, etc. allows OCT scanning to be applied to a region that almost coincides with the second three dimensional region. Hereinafter, the ophthalmic apparatus 100 configured as described above will be described in more detail.

As shown in FIG. 1, the ophthalmic apparatus 100 includes the light source 102 that generates a light beam. The light source 102 is, for example, a broadband light source or a wavelength tunable light source. The beam splitter (BS) 104 splits the light beam emitted from the light source 102 into a sample light beam (measurement light) and a reference light beam (reference light). In other words, the beam splitter 104 directs part of the light beam emitted from the light source 102 to the sample arm 106 and another part to the reference arm 108.

The reference arm 108 includes the polarization controller 110 and the collimator 112. The polarization controller 110 is used for regulating the reference light beam, for example, for maximizing the interference efficiency. The collimator 112 outputs the reference light beam as a collimated light beam (parallel light beam). The reference light beam output from the collimator 112 is converted into a convergent light beam by the lens 114 and projected onto the reflecting mirror 115. The reference light beam reflected by the reflecting mirror 115 returns to the beam splitter 104 through the reference arm 108. The lens 114 and the reflecting mirror 115 are movable together, whereby the distance from the collimator 112 is changed (in other words, the path length of the reference light beam is changed).

The sample arm 106 guides the sample light beam via the collimator 117, the two dimensional scanner 116, and one or more objective lenses 118, and projects the sample light beam onto the eye 120 as a sample. The two dimensional scanner 116 is, for example, a galvano mirror scanner or a micro electro mechanical systems (MEMS) scanner. The return light of the sample light beam projected on the eye 120 returns to the beam splitter 104 through the sample arm 106. The two dimensional scanner 116 enables OCT scanning on a three dimensional region of the eye 120.

The beam splitter 104 generates an interference light beam by superposing the return light of the reference light beam and the return light of the sample light beam with one another. The interference light beam is guided to the detector 122 and detected by it. With this, the echo time delay of the light is measured from the interference spectrum.

The detector 122 generates a plurality of output sets, based on the composition (superposition) of the return light of the sample light beam supplied from the sample arm 106 and the return light of the reference light beam supplied from the reference arm 108. The result of the composition is interferogram data. For example, the plurality of output sets generated by the detector 122 may respectively correspond to light intensities received at different wavelengths output from the light source 102. When the sample light beam is projected sequentially to a plurality of XY positions by the two dimensional scanner 116, the light intensities detected include information, for the XY positions, on reflection intensity distributions (backscattering intensity distributions) from the inside region of the eye 120 along the depth direction (Z direction).

A three dimensional data set is obtained in the above-described manner. The three dimensional data set includes a plurality of pieces of A-scan data respectively corresponding to the XY positions. Each piece of A-scan data represents a spectral intensity distribution at a corresponding XY position. The three dimensional data set acquired by the detector 122 is sent to the processing device 124.

The processing device 124 is configured, for example, to perform creation of a two dimensional map based on the three dimensional data set, designation of a region to which an OCT scan is applied based on the two dimensional map, and generation of image data from a three dimensional data set acquired from the designated region by the OCT scans. The processing device 124 includes a processor that operates according to a processing program. Some specific examples of the processing device 124 will be described later.

The controlling device 126 executes control of each part of the ophthalmic apparatus 100. For example, the controlling device 126 performs various kinds of control for applying an OCT scan to a region of the eye 120 designated in advance. The controlling device 126 includes a processor that operates according to a control program. Some specific examples of the controlling device 126 will be described later.

Although not shown in the drawings, the ophthalmic apparatus 100 may further include a display device, an operation device, a communication device, and other elements.

Further description of the processing device 124 and the controlling device 126 will be given with referring to FIG. 2. The processing device 124 includes the map creating unit 202, the region designating unit 204, and the image data generating unit 206. The controlling device 126 includes the scan controlling unit 210.

The OCT scanner 220 shown in FIG. 2 applies an OCT scan to the sample (the eye 120). The OCT scanner 220 of the present aspect includes, for example, the group of optical elements shown in FIG. 1, namely, the light source 102, the beam splitter 104, the sample arm 106 (the collimator 117, the two dimensional scanner 116, the objective lens 118, etc.), the reference arm 108 (the collimator 112, the lens 114, the reflecting mirror 115, etc.), and the detector 122. In some aspects, the OCT scanner may have other configurations.

The controlling device 126 executes control of each part of the ophthalmic apparatus 100. Control relating to OCT scanning, among various kinds of control, is performed by the scan controlling unit 210. The scan controlling unit 210 of the present aspect is configured to perform control for the OCT scanner 220. For example, the scan controlling unit 210 of the present aspect may be configured to perform at least control for the light source 102, control for the two dimensional scanner 116, and movement control for the lens 114 and the reflecting mirror 115. The scan controlling unit 210 includes a processor that operates according to a scan controlling program.

The processing device 124 executes various kinds of data processing (e.g., calculation, analysis, measurement, image processing, etc.). The map creating unit 202, the region designating unit 204, and the image data generating unit 206 respectively perform the three processes described above; namely, the creation of a two dimensional map based on the three dimensional data set, the designation of a region to which an OCT scan is applied based on the two dimensional map, and the generation of image data from a three dimensional data set acquired from the region designated by the OCT scan.

The map creating unit 202 includes a processor that operates according to a map creating program. The region designating unit 204 includes a processor that operates according to a region designating program. The image data generating unit 206 includes a processor that operates according to an image data generating program.

The map creating unit 202 receives three dimensional data acquired from the eye 120 by an OCT scan, from the OCT scanner 220. The OCT scan is performed by the OCT scanner 220 under the control of the scan controlling unit 210, targeting the first three dimensional region of the eye 120 designated in advance. With the OCT scan, the first three dimensional data set is acquired and supplied to the map creating unit 202.

The map creating unit 202 creates the first two dimensional map based on representative intensity values respectively of the plurality of pieces of A-scan data included in the first three dimensional data set. The first three dimensional data set is data before being subjected to an imaging process (e.g., Fourier transform) by the image data generating unit 206. The A-scan data is a spectral intensity distribution.

The processes performed by the map creating unit 202 may be processes on the basis of the technique disclosed in the above-mentioned Japanese Patent No. 6,230,023 (US Patent Application Publication No. 2014/0293289). In brief, the technique includes the following steps: a step of applying a high pass filter to A-scan data representing a spectral intensity distribution corresponding to a specific XY position, to extract its amplitude component; and a step of determining a single estimated intensity value (representative intensity value) from the extracted amplitude component based on the inverse cumulative distribution function (inverse CDF).

Figure 5:
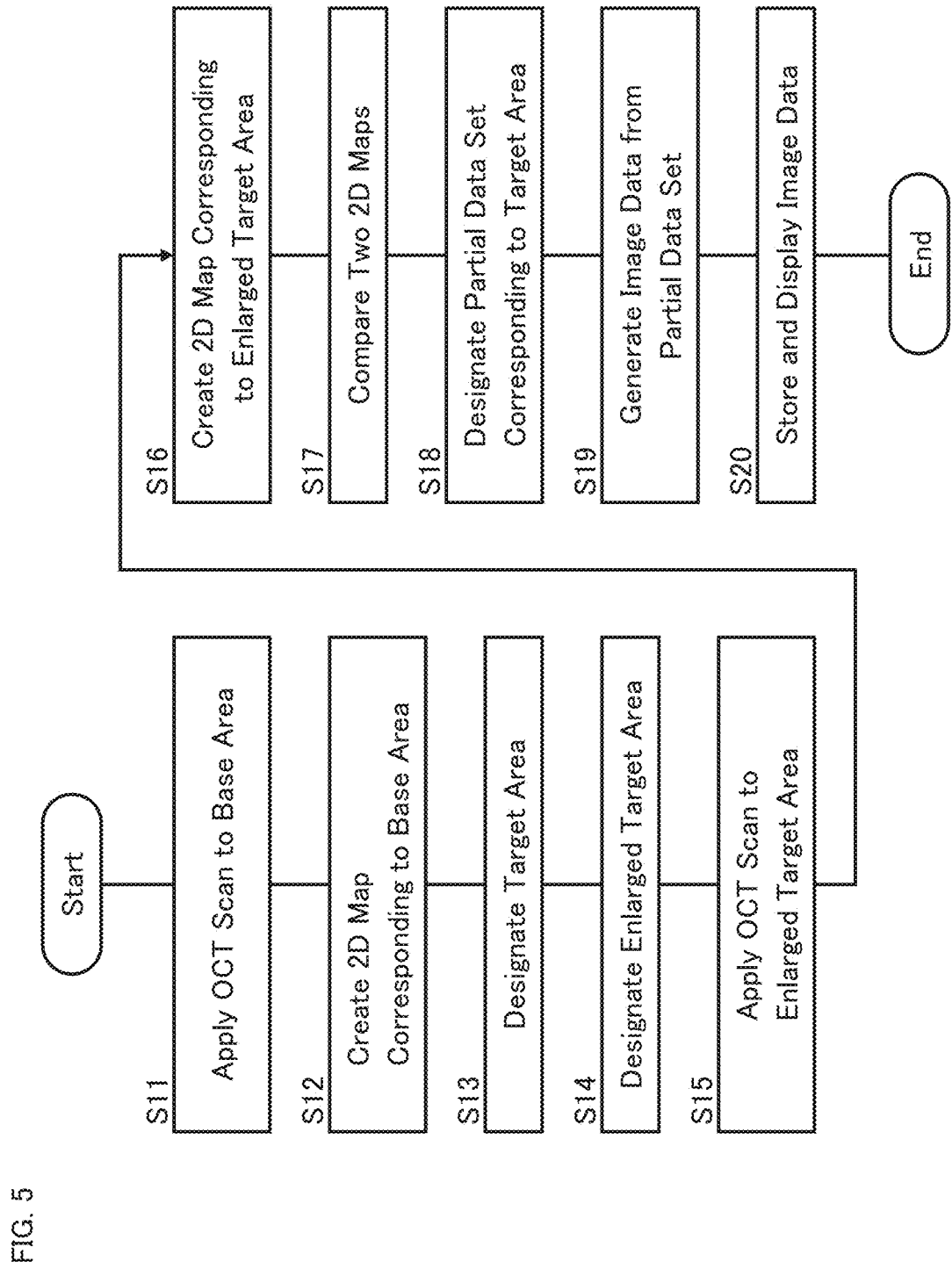
FIG. 5 is a flowchart illustrating the operation of the ophthalmic apparatus according to the exemplary aspect.

More specifically, as described in FIG. 5 of Japanese Patent No. 6,230,023 (US Patent Application Publication No. 2014/0293289) and the description thereof, the map creating unit 202 in some aspects may be configured to execute the following steps: a step of applying high pass filtering to A-scan data; a step of applying down-sampling to the filtered A-scan data (or a step of truncating the filtered A-scan data); a step of squaring the down-sampled A-scan data (or a step of taking an absolute value of the down-sampled A-scan data); a step of sorting the results of the squaring (or a step of selecting a quantile); a step of performing calculation using the inverse CDF method; and a step of determining a single estimated intensity value (representative intensity value) from the result of the calculation.

In some other aspects, the map creating unit 202 may be configured to execute the following steps: a step of applying high pass filtering to A-scan data; a step of applying down-sampling to the filtered A-scan data (or a step of truncating the filtered A-scan data); a step of squaring the down-sampled A-scan data (or a step of taking an absolute value of the down-sampled A-scan data); a step of selecting the largest percentile value in the result of the squaring; and a step of determining a single estimated intensity value (representative intensity value) from the largest percentile value selected.

In still some other aspects, the map creating unit 202 may be configured to perform the following steps: a step of applying high pass filtering to A-scan data; a step of applying down-sampling to the filtered A-scan data (or a step of truncating the filtered A-scan data); a step of selecting the smallest and largest percentile values from the down-sampled A-scan data; a step of squaring each of the smallest and largest percentile values selected (or a step of taking an absolute value of each of the smallest and largest percentile values selected); and a step of combining the squared smallest percentile value and the squared largest percentile value (e.g., calculating their average, or selecting a preset percentile value using the inverse CDF method).

For details of the map creating technique exemplified above, Japanese Patent No. 6,230,023 (US Patent Application Publication No. 2014/0293289) may be referred to. Further, applicable map creating techniques are not limited to the above-described examples, and any technique within the scope of the disclosure in Japanese Patent No. 6,230,023 (US Patent Application Publication No. 2014/0293289) or any modification thereof may be applied.

Representative intensity values corresponding to the XY positions may be obtained by applying a series of steps as described above to each A-scan data in the first three dimensional data set. The first two dimensional map representing the distribution of the representative intensity values in the XY plane may be created by mapping the correspondence relationships between the XY positions and the representative intensity values obtained by the series of steps.

Although some cases of creating the first two dimensional map from the first three dimensional data set have been described herein, the same or like processes may be applied to cases where other two dimensional maps are created from other three dimensional data sets.

The first two dimensional map created by the map creating unit 202 is input to the region designating unit 204. The region designating unit 204 designates the second three dimensional region of the eye 120 based on the first two dimensional map.

For example, the region designating unit 204 is configured to analyze the first two dimensional map to detect an image of a predetermined site of the eye 120, and designate the second three dimensional region so that the detected image is placed in a predetermined position within the scan area. The predetermined site may be, for example, any of the followings: lesion; blood vessel; optic nerve head; macula; sub-tissue of eye fundus (e.g., inner limiting membrane, nerve fiber layer, ganglion cell layer, inner plexiform layer, inner nuclear layer, outer plexiform layer, outer nuclear layer, external limiting membrane, photoreceptor layer, retinal pigment epithelium layer, Bruch membrane, choroid, sclera, etc.); sub-tissue of cornea, (e.g., corneal epithelium, Bowman's membrane, corneal stroma, Dua's layer, Descemet's membrane, corneal endothelium, etc.); iris; crystalline lens; Zinn's zonule; ciliary body: vitreous body; and other ocular tissues. Any image processing technique may be applied to the detection of the image of the predetermined site. For example, any image classification method, any image detection method, any image recognition method, any image segmentation method, any deep learning method, and/or other methods may be applied. As an example, the region designating unit 204 may analyze the first two dimensional map created from the first three dimensional data set acquired by applying OCT scanning to the fundus to detect an image of the optic nerve head. Then, the region designating unit 204 may designate the second three dimensional region so that the optic nerve head image detected is located in the central region of the scan area.

In another example, the controlling device 126 displays the first two dimensional map on the display device (not shown in the drawings). The user designates a desired region in the first two dimensional map displayed, using an operation device (not shown in the drawings). The region designating unit 204 may designate the second three dimensional region based on the region designated in the first two dimensional map. For example, the region designating unit 204 may designate the region designated by the user as the second three dimensional region. Alternatively, the region designating unit 204 may designate the region designated by the user as a target region (also referred to as a target area; described later), and further designate the second three dimensional region based on the target region.

The data usable for the designation of the second three dimensional region is not limited to the first two dimensional map. For example, any of data generated from the first two dimensional map, data used in a process prior to the creation of the first two dimensional map, and data generated from this data may be referred to for the designation of the second three dimensional region. Here, the data used in a process prior to the first two dimensional map creation may be the first three dimensional region or the first three dimensional data set.

Further, the size of the second three dimensional region may be the same as or different from that of the first three dimensional region. For example, the size of the second three dimensional region may be set larger than that of the first three dimensional region. Furthermore, the shape of the second three dimensional region may be the same as or different from that of the first three dimensional region. In addition, the orientation of the second three dimensional region may be the same as or different from that of the first three dimensional region.

Some examples of processing for designating the second three dimensional region will be described. In some examples, the first three dimensional region is typically set to be sufficiently wide. For example, the first three dimensional region is set to the maximum scan area with the two dimensional scanner 116 of the ophthalmic apparatus 100. With this, the subsequent processes may refer to a wide region of the eye 120. Hereinafter, the first three dimensional region (typically, the XY region corresponding thereto) may be referred to as a "base area".

Figure 3A:
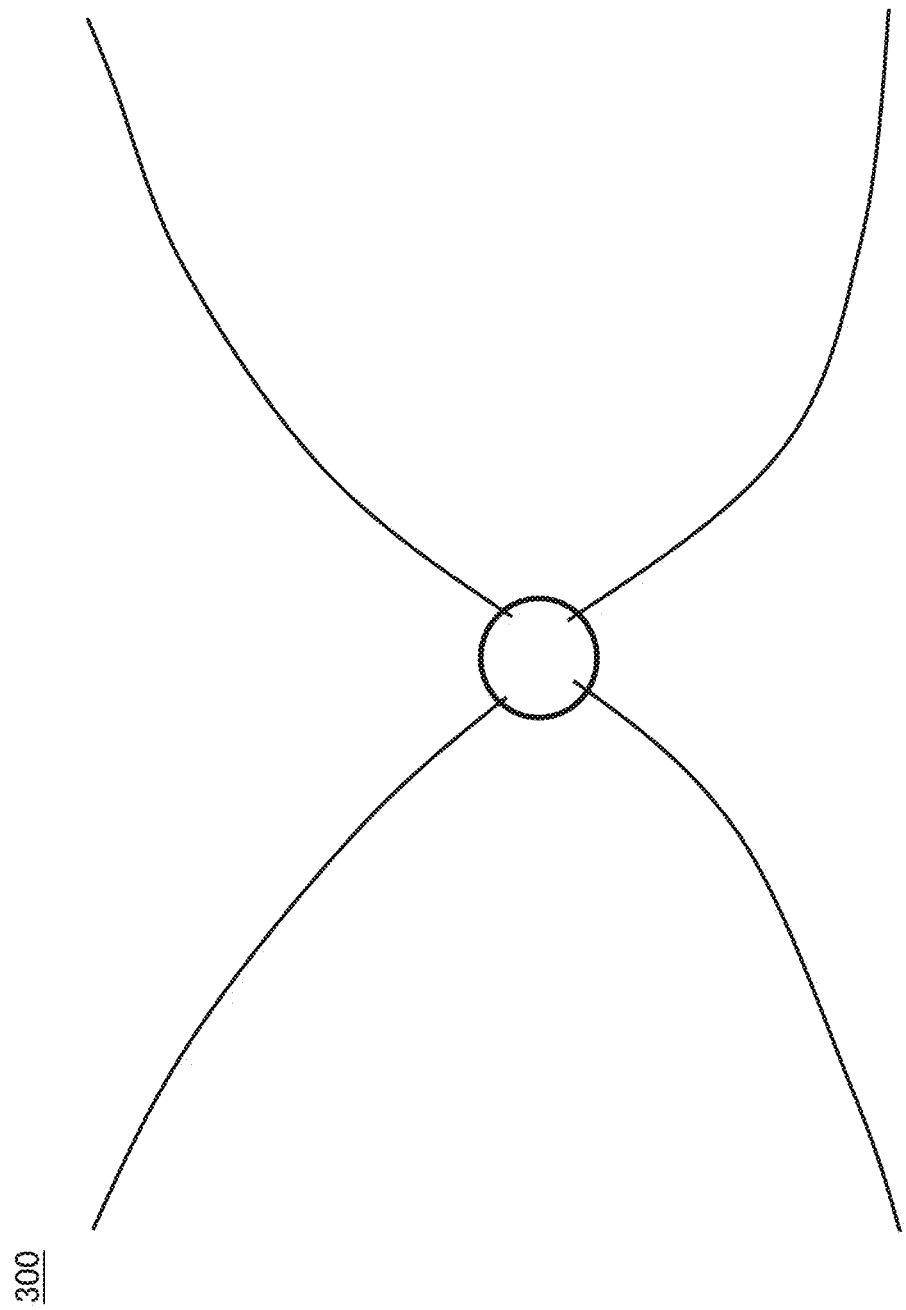
FIG. 3A is a schematic diagram for describing processing performed by the ophthalmic apparatus according to the exemplary aspect.
Figure 3B:
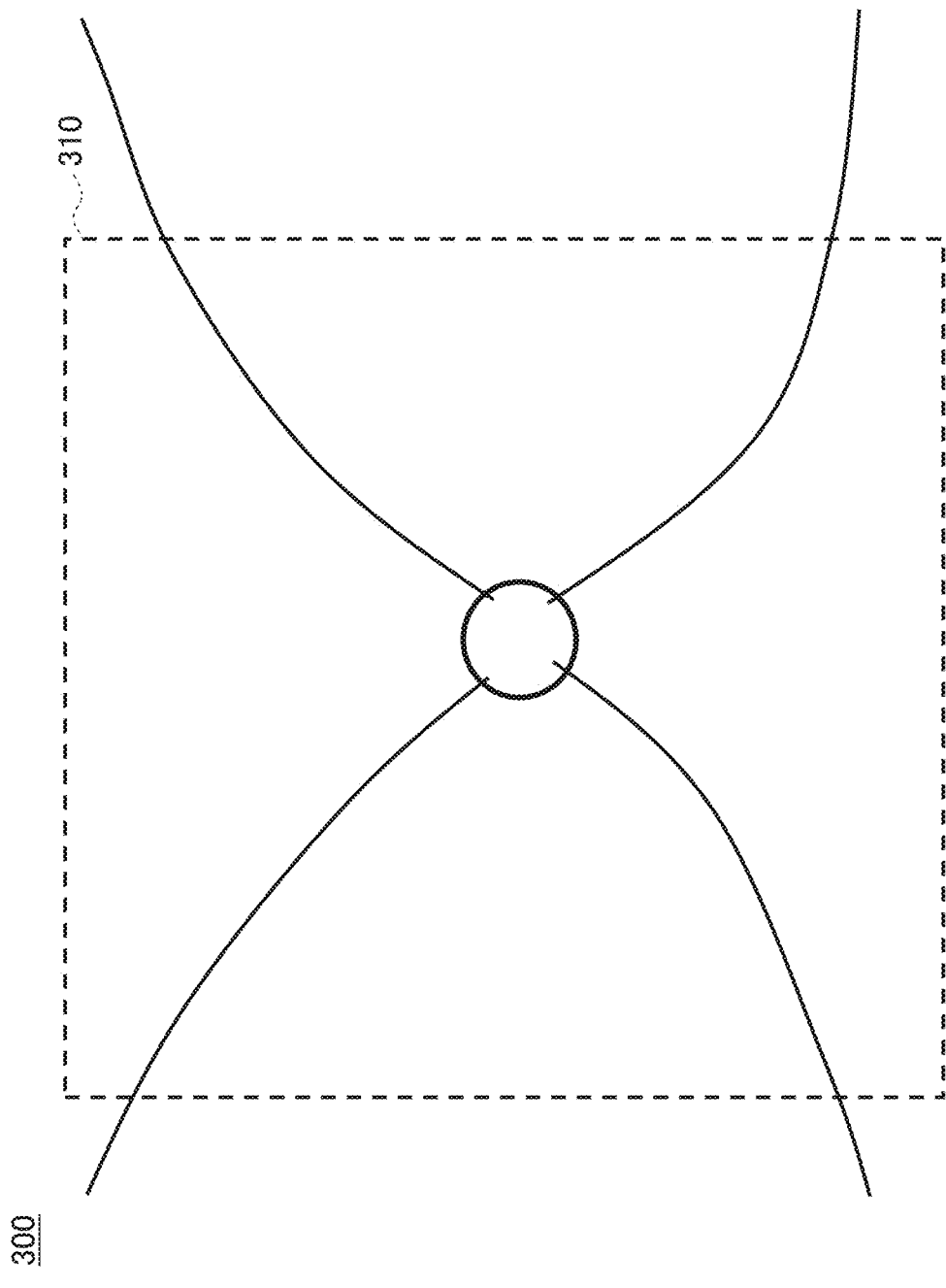
FIG. 3B is a schematic diagram for describing processing performed by the ophthalmic apparatus according to the exemplary aspect.

FIG. 3A shows the fundus 300 (an image seen from the front). FIG. 3B shows an exemplary base area (the first three dimensional region) 310 set for the fundus 300. The ophthalmic apparatus 100 applies an OCT scan to the fundus 300 targeting the base area 310 to acquire the first three dimensional data set. The map creating unit 202 creates the first two dimensional map from the first three dimensional data set acquired.

Figure 3C:
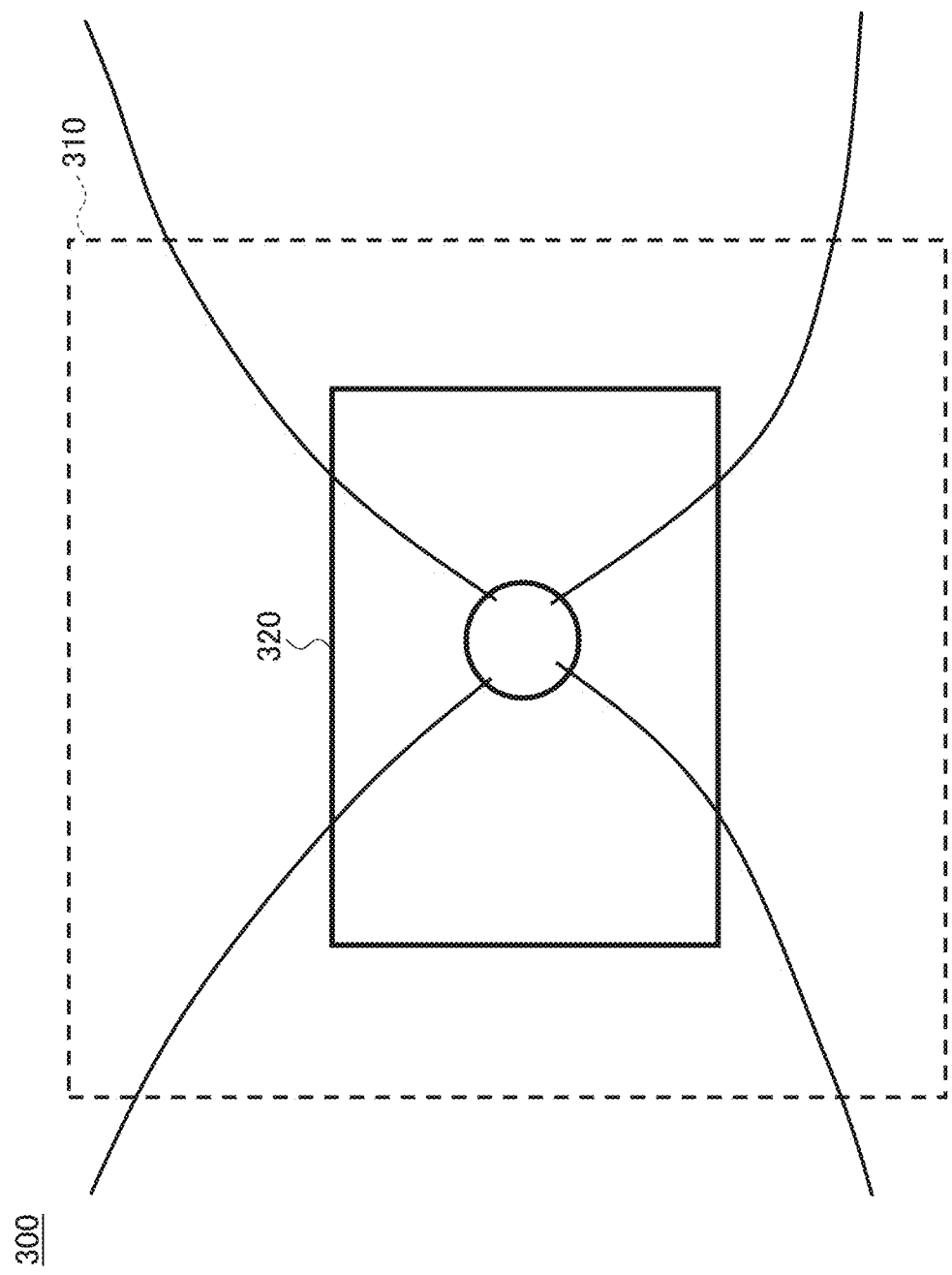
FIG. 3C is a schematic diagram for describing processing performed by the ophthalmic apparatus according to the exemplary aspect.

In the present example, the region designating unit 204 first designates a region of the fundus 300 (target area) to be referred to in the subsequent processes, tasks or operations (e.g., archiving, analysis, diagnosis, evaluation, research) based on the first two dimensional map corresponding to the base area 310. The target area is a desired region of the fundus 300 and is a three dimensional region included in the base area 310. The target area 320 shown in FIG. 3C is set within the base area 310.

As described above, the target area designation is performed automatically or based on the user's operation. In the latter case, automatic processes may optionally be performed to support the user's operation. Such automatic processes may be the detection of a predetermined site of the fundus 300, and the display of an image of the detected site or an image representing the location of the detected site.

Figure 3D:
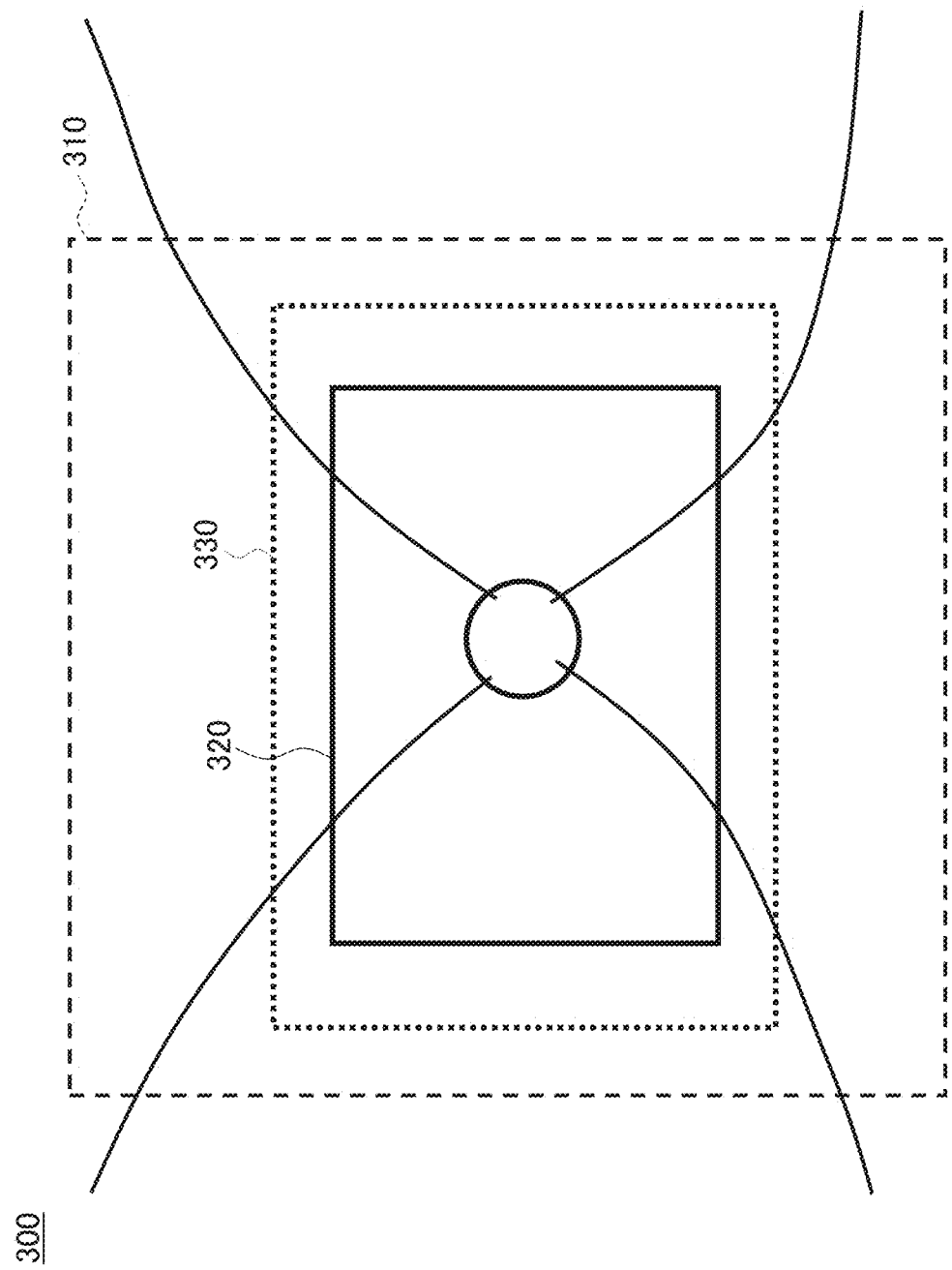
FIG. 3D is a schematic diagram for describing processing performed by the ophthalmic apparatus according to the exemplary aspect.

Furthermore, the region designating unit 204 in the present example designates the second three dimensional region in such a way that the second three dimensional region includes the target area designated. For example, the second three dimensional region is designated in such a way that the second three dimensional region includes the target area and is included in the base area. The second three dimensional region designated in such a way may be referred to as an "enlarged target area". The enlarged target area 330 shown in FIG. 3D is designated to include the target area 320 and to be included in the base area 310.

The size of the enlarged target area may be any of the followings: a predetermined size; a size determined based on the target area; a size determined based on the base area; and a size determined based on both the target area and the base area. The size of the enlarged target area is calculated, for example, by multiplying the size of the target area by a predetermined magnification factor (the magnification factor exceeding 1), or by adding a margin of a predetermined size to the size of the target area.

The shape of the enlarged target area may be any of the followings: a predetermined shape; a shape determined based on the target area; a shape determined based on the base area; and a shape determined based on both the target area and the base area. For example, the shape of the enlarged target area is the same as that of the target area.

The image data generating unit 206 generates image data based on data acquired by the OCT scanner 220. For example, the image data generating unit 206 constructs image data of a cross sectional image of the eye 120 based on the output from the OCT scanner 220. The output is referred to as sampling data or interference signal data. Such image data generating processing includes filtering, fast Fourier transform (FFT) etc. as in conventional OCT techniques (e.g., swept source or spectral domain OCT technique). With such processing, reflection intensity profiles are acquired for the A-lines respectively corresponding to the XY positions, and a group of image data for the A-lines is constructed by performing imaging process on the reflection intensity profiles. Here, an A-line is a scan path of the measurement light beam in the eye 120, and a reflection intensity profile lies along the Z direction. Further, image data for an A-line is referred to as A-scan image data.

Furthermore, the image data generating unit 206 may be configured to construct two dimensional image data or three dimensional image data, by constructing a plurality of pieces of A-scan image data according to the mode of the OCT scan, and then arranging these A-scan image data. The OCT scan mode is concerned with, for example, the deflection of the measurement light beam and the movement of the A-scan position.

In the case where a plurality of pieces of cross sectional image data is obtained by raster scan or another scan mode, the image data generating unit 206 may construct stack data by embedding the plurality of pieces of cross sectional image data in a single three dimensional coordinate system. In addition, the image data generating unit 206 may construct voxel data (volume data) by applying voxelization to the stack data.

The image data generating unit 206 may be configured to perform rendering on the stack data or volume data. A rendering technique applied thereto is optional. For example, any of volume rendering, multi planar reconstruction (MPR), surface rendering, and other rendering techniques may be applied thereto. Furthermore, the image data generating unit 206 may be configured to construct a planar image from the stack data or volume data. Examples of the planar image include a front image and en-face image. For example, the image data generating unit 206 may be configured to construct a projection image by integrating the stack data or volume data along their A-lines.

In the present example, the ophthalmic apparatus 100 applies an OCT scan targeting the second three dimensional region designated by the region designating unit 204 to acquire the second three dimensional data set. Here, the second three dimensional region may be the enlarged target area. The image data generating unit 206 generates image data from at least part of the second three dimensional data set. For example, in the case where the second three dimensional data set corresponding to the enlarged target area 330 is acquired, the image data generating unit 206 may extract part corresponding to the target area 320, which is part of the enlarged target area 330, from the second three dimensional data set, and then generate image data from the partial data set extracted.

The processing device 124 may be capable of performing various kinds of data processing other than the data processing described above. The processing device 124 may be configured to process data acquired by an OCT scan (referred to as OCT data). The OCT data is, for example, interference signal data, reflection intensity profiles, or image data. Note that the interference signal data is at least part of the three dimensional data set.

The processing device 124 may be capable of processing data other than OCT data. For example, in the event that the ophthalmic apparatus 100 includes a data acquisition device other than the OCT scanner 220, the processing device 124 may be configured to process the data acquired by the data acquisition unit. An ophthalmic apparatus adoptable to the data acquisition unit may be any ophthalmic imaging apparatus such as a fundus camera, scanning laser ophthalmoscope (SLO), surgical microscope, or slit lamp microscope. An ophthalmic apparatus adoptable to the data acquisition unit may be any ophthalmic measurement apparatus such as a refractometer, keratometer, tonometer, eye axial length measurement device, specular microscope, wave front analyzer, or perimeter. Further, in the event that the OCT apparatus is a medical apparatus of any kind, that is, in the event that the OCT apparatus is an apparatus used in any medical department, the medical apparatus adopted as the data acquisition unit may be an medical imaging apparatus of any kind and/or medical examination apparatus of any kind. In addition, an OCT apparatus used in any field other than medical care includes a data acquisition unit corresponding to the field.

Several examples of the operation of the ophthalmic apparatus 100 will be described.

Figure 4:
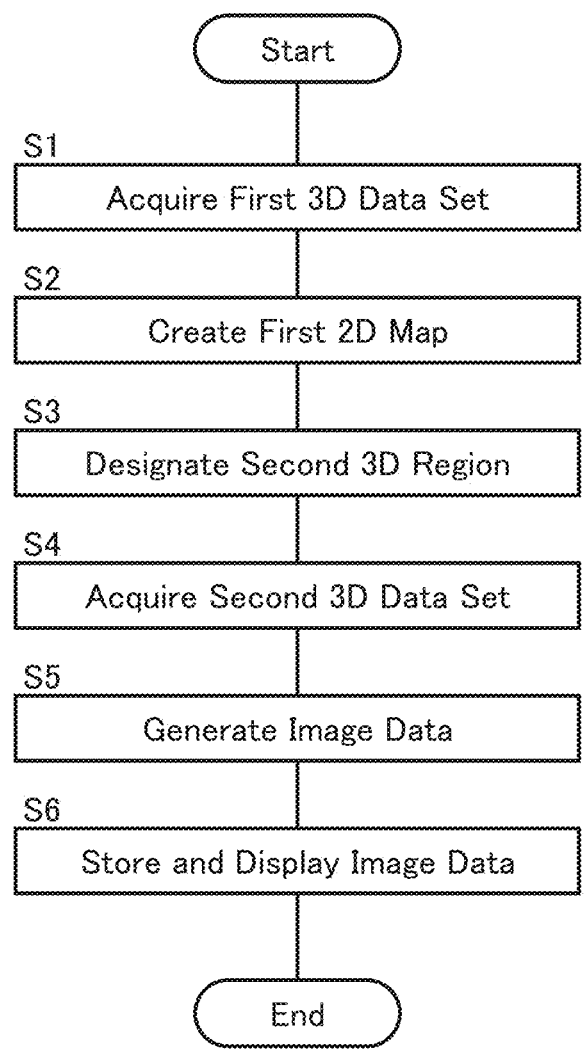
FIG. 4 is a flowchart illustrating the operation of the ophthalmic apparatus according to the exemplary aspect.

The first operation example will be described with referring to FIG. 4. The present example begins with that the scan controlling unit 210 controls the OCT scanner 220 to apply, to the eye 120, an OCT scan targeting the first three dimensional region designated in advance, in order to acquire the first three dimensional data set (S1). For example, the scan controlling unit 210 controls the OCT scanner 220 to apply an OCT scan to the fundus 300 targeting the base area 310 designated in advance, and acquire the first three dimensional data set.

Next, the map creating unit 202 creates the first two dimensional map based on representative intensity values respectively of the plurality of pieces of A-scan data included in the first three dimensional data set acquired in step S1 (S2). For example, the map creating unit 202 creates the first two dimensional map based on representative intensity values respectively of the plurality of pieces of A-scan data included in the first three dimensional data set corresponding to the base area 310.

Next, the region designating unit 204 designates the second three dimensional region of the eye 120 based at least on the first two dimensional map created in step S2 (S3). For example, the region designating unit 204 designates the target area 320 and the enlarged target area 330 of the fundus 300 based at least on the first two dimensional map corresponding to the base area 310.

Next, the scan controlling unit 210 controls the OCT scanner 220 to apply an OCT scan targeting the second three dimensional region designated in step S3, and acquire the second three dimensional data set (S4). For example, the scan controlling unit 210 controls the OCT scanner 220 to apply an OCT scan targeting the enlarged target area 330 in order to acquire the second three dimensional data set.

Next, the image data generating unit 206 generates image data from at least part of the second three dimensional data set acquired in step S4 (S5). For example, the image data generating unit 206 generates image data from a partial data set corresponding to the target area 320. Here, the partial data set is a subset of the second three dimensional data set that corresponds to the enlarged target area 330.

Next, the controlling device 126 may be configured to display the image data generated in step S5 on a display device (not shown in the drawings) (S6). The display device may be an element of the ophthalmic apparatus 100, a peripheral device of the ophthalmic apparatus 100, or a device connectable to the ophthalmic apparatus 100 via a communication line such as a device for telemedicine.

Further, the controlling device 126 may be configured to store the image data generated in step S5 in a storage device (not shown in the drawings) (S6). The storage device may be an element of the ophthalmic apparatus 100, a peripheral device of the ophthalmic apparatus 100, a device connectable to the ophthalmic apparatus 100 via a communication line, or a portable recording medium.

The second operation example will be described with referring to FIG. 5. The following description refers to the example shown in FIG. 3A to FIG. 3D.

First, the scan controlling unit 210 controls the OCT scanner 220 to acquire a three dimensional data set by applying an OCT scan to the fundus 300 targeting the base area 310 designated in advance (S11). The three dimensional data set acquired in such a way is referred to as a base data set.

Next, the map creating unit 202 creates a two dimensional map based on representative intensity values respectively of the plurality of pieces of A-scan data included in the base data set acquired in step S11 (S12). The two dimensional map created from the base data set is referred to as a base map.

Then, the region designating unit 204 designates the target area 320 of the fundus 300 based at least on the base map created in step S12 (S13).

Subsequently, the region designating unit 204 designates the enlarged target area 330 based at least on the target area 320 designated in step S13 (S14).

Next, the scan controlling unit 210 controls the OCT scanner 220 to acquire a three dimensional data set by applying an OCT scan targeting the enlarged target area 330 designated in step S14 (S15). The three dimensional data set acquired in such a way is referred to as an enlarged target data set.

Next, the map creating unit 202 creates a two dimensional map based on representative intensity values respectively of the plurality of pieces of A-scan data included in the enlarged target data set acquired in step S15 (S16). The two dimensional map created from the enlarged target data set is referred to as an enlarged target map.

Subsequently, the image data generating unit 206 makes a comparison between the base map created in step S12 and the enlarged target map created in step S16 (S17).

The comparison of the two dimensional maps may include an image correlation calculation. One of the techniques adoptable to the image correlation calculation is described in Japanese Patent No. 6,276,943 (International Patent Publication No. WO2015/029675). In the case where this technique is employed, the image data generating unit 206 may be configured to apply phase only correlation (POC) to the set of the base map (or, part thereof corresponding to the enlarged target map) and the enlarged target map in order to calculate a positional difference amount (amount of misalignment, position aberration, positional gap, mutual deviation, or the like) between the base map and the enlarged target map. The positional difference amount includes, for example, any one or both of a translation amount and a rotation amount.

For details of such a two dimensional map comparing technique with phase only correlation, Japanese Patent No. 6,276,943 (International Patent Publication No. WO2015/029675) may be referred to. Further, the two dimensional map comparing technique adopted hereto is not limited to the above-described example, and any technique within the scope of the invention described in Japanese Patent No. 6,276,943 (International Patent Publication No. WO2015/029675) or any modification thereof may be applied hereto.

Furthermore, any kinds of image correlation other than phase only correlation may be used, and further any kinds of image comparison other than image correlation may be used, in order to implement the two dimensional map comparison of the present example.

An example of the two dimensional map comparison executed in step S17 will be described with referring to FIG. 6. As described above, any one or both of the location and orientation of the fundus 300 (the eye 120) is generally different between the points of time when the OCT scans are performed in steps S11 and S15. The two dimensional map comparison in step S17 is performed to detect the difference between the two dimensional maps, that is, the difference the scanned region, due to the location difference and/or orientation difference.

As described above, the present example is configured to compare the base map created in step S12 and the enlarged target map created in step S16 with each other. In other words, the base area 610 (310) and the area (scan application area) 630 to which the OCT scan is applied in step S15 are compared with each other. Put further differently, the enlarged target area 330 and the scan application area 630 to which the OCT scan based thereon is applied are compared with each other.

As can be seen from the comparison between FIG. 3D and FIG. 6, the scan application area 630 translates in the upper left direction and rotates in the clockwise direction with respect to the enlarged target area 330. The present example calculates the translation amount and the rotation amount of the scan application area 630 with respect to the enlarged target area 330 by the comparison between the base map and the enlarged target map.

Next, the image data generating unit 206 designates a partial data set corresponding to the target area 320 in the enlarged target data set acquired in step S15, based on the result of the two dimensional map comparison executed in step S17 (S18). The partial data set is part of the three dimensional data set corresponding to the scan application area 630, and is a data set corresponding to the target area 620 (320).

Next, the image data generating unit 206 generates image data from the partial data set designated in step S18 (S19). With this, the image data that corresponds to the target area 620 (320) is obtained. In other words, the image data corresponding to the region of the fundus 300 to be referred to in the post-stage processes, tasks, and/or operations as described above may be obtained.

Subsequently, the controlling device 126 may display the image data generated in step S19 on a display device (not shown in the drawings) (S20). Further, the controlling device 126 may store the image data generated in step S19 in a storage device (not shown in the drawings) (S20).

The third operation example will be described. In the second operation example, it is assumed that the scan application area 630 includes the target area 620. However, there may be cases in which the scan application area 630 does not include the target area 620. The present example describes, with referring to FIG. 7, an operation taking into consideration the case where the scan application area 630 does not include the target area 620. In the following, reference is also made to FIG. 3A to FIG. 3D and FIG. 6.

Steps S31 to S37 of the flowchart shown in FIG. 7 are the same as steps S11 to S17 of the flowchart shown in FIG. 5, respectively.

In step S38 of the present example, the image data generating unit 206 determines whether or not the area to which the OCT scan is applied (the scan application area) in step S35 includes the target area designated in step S33. Here, the determination is carried out based (at least) on the result of the comparison executed in step S37 between the base map (the two dimensional map created in step S32) and the enlarged target map (the two dimensional map created in step S36).

In other words, the image data generating unit 206 determines whether or not the three dimensional data set acquired by the OCT scan in step S35 (the enlarged target data set) includes the three dimensional data set corresponding to the target area (the target data set), based (at least) on the result of the comparison in step S37.

An example of processing applicable to the determination in step S38 will be described. As mentioned above, the comparison in step S37 may include the image correlation calculation, and the result of the comparison may include the positional difference amount (e.g., translation amount and/or rotation amount) between the base map and the enlarged target map.

Since steps S33 designates the target area with respect to the base map, the positional relationship between the base area and the target area is known.

Further, step S37 obtains the positional difference amount between the base map (the base area) and the enlarged target map (the scan application area) by comparing the two maps with one another.

Combining these items derives the positional relationship between the scan application area and the target area. That is, the positional relationship between the enlarged target data set and the target data set (in an image space) is obtained.

The image data generating unit 206 may determine whether or not the scan application area includes the target area based on the positional relationship obtained in this manner. That is, the image data generating unit 206 may determine whether or not the enlarged target data set includes the target data set. Note that processing applicable to the determination in step S38 is not limited to the present example.

FIG. 6 illustrates an aspect in the case where the scan application area includes the target area. In the event that the scan application area is determined to include the target area (S38: Yes), the image data generating unit 206 designates a partial data set (target data set) corresponding to the target area 320 in the enlarged target data set acquired in step S35 (S39), and then generates image data from the target data set (S40). The controlling device 126 may display the image data on a display device (not shown in the drawings) or store the image data in a storage device (not shown in the drawings) (S41).

On the other hand, FIG. 8 shows an example of an aspect in the case where the scan application area does not include the target area. In the example shown in FIG. 8, part of the target area 820 set within the base area 810 (310) is located outside the scan application area 830.

In the event that the scan application area is determined not to include the target area, the scan controlling unit 210 controls the OCT scanner 220 to apply another OCT scan targeting an enlarged target area to acquire a new enlarged target data set. The enlarged target area adopted to the another OCT scan may be the same as the enlarged target area adopted to the previous (or earlier) OCT scan. Alternatively, any one or more of the position, size, shape and orientation of the enlarged target area adopted to the another OCT scan may be different from that of the previous (or earlier) OCT scan. The series of processes as described above may be repeated until the scan application area is determined to include the target area. The image data generating unit 206 generates image data from at least part of the new enlarged target data set (typically, from a partial data set corresponding to the target data set) in the event that the scan application area is determined to include the target area.

In the present example, the processing returns to step S34 in the event that the scan application area is determined not to include the target area (S38: No). The region designating unit 204 designates a new enlarged target area based at least on the target area designated in step S33 (and on the base map created in step S32) (S34).

Note that the processing may be returned to step S33 in the event that the scan application area is determined not to include the target area (S38: No). If this is the case, a new target area is designated (S33), and a new enlarged target area is designated to include the new target area (and to be included in the base area) (S34).

Several examples of the process of the new enlarged target area designation will be described. The region designating unit 204 may designate a new enlarged target area based on the result of the comparison in step S37. For example, in the event that the result of the comparison includes a positional difference amount (translation amount and/or rotation amount), the region designating unit 204 may designate a new enlarged target area to compensate (or, cancel or eliminate) the positional difference amount. Typically, if the positional difference amount obtained by the comparison is the positional difference amount of the previous enlarged target area with respect to the target area, the region designating unit 204 may designate a new enlarged target area by moving the previous enlarged target area by the inverse amount of the positional difference amount. The new enlarged target area includes the target area (and is included in the base area).

As another example, the region designating unit 204 may be configured to designate a new enlarged target area to include the target area (and to be included in the base area) by increasing the size of the enlarged target area based on the positional difference amount obtained by the comparison.

Further, as another example, the region designating unit 204 may be configured to designate a new enlarged target area to include the target area (and to be included in the base area) by changing the shape of the enlarged target area based on the positional difference amount obtained by the comparison.

Furthermore, as another example, the region designating unit 204 may be configured to designate a new enlarged target area to include the target area (and to be included in the base area) by changing the orientation of the enlarged target area based on the positional difference amount obtained by the comparison.

Combining these examples, the region designating unit 204 may be configured to designate a new enlarged target area to include the target area (and to be included in the base area) by changing any one or more of the location, size, shape and orientation of the enlarged target area on the basis of the positional difference amount obtained by the comparison.

After the designation of the new enlarged target area, the scan controlling unit 210 controls the OCT scanner 220 to acquire a new enlarged target data set by applying an OCT scan targeting the new enlarged target area (S35). Next, the map creating unit 202 creates a new enlarged target map corresponding to the new enlarged target area designated in step 34, based on the new enlarged target data set (S36). Subsequently, the image data generating unit 206 compares the new enlarged target map created in step S36 with the base map created in step S32 (S37). Then, the image data generating unit 206 determines whether or not the scan application area corresponding to the new enlarged target map includes the target area (S38). Here, the scan application area corresponding to the new enlarged target map is the area on which the OCT scan targeting the new enlarged target area is performed in step S35.

Such a series of processes described thus far is repeatedly executed until the determination in step S38 reaches "Yes". Note that error determination may be performed by setting the upper limit of the number of repetitions or setting the upper limit of the repetition time.

In the event that the scan application area is determined to include the target area (S38: Yes), the image data generating unit 206 designates a partial data set (target data set) corresponding to the target area 320 of the new enlarged target data set acquired in step S35 (S39), and then generates image data from the target data set (S40). The controlling device 126 may display the image data generated on a display device (not shown in the drawings) or store the image data generated in a storage device (not shown in the drawings) (S41).

The above example is configured to carry out the determination of whether or not the scan application area includes the entire target area; however, the modes of determination adopted to step S38 is not limited to this. For example, the determination may be of whether or not a partial area of a predetermined ratio of the target area is included in the target area.

Alternatively, an area of interest corresponding to a site of interest may be designated in the target area, and then the determination may be of whether or not at least the area of interest is included in the scan application area. Here, the designation of the area of interest is performed manually or automatically. The automatic designation includes, for example, a process of detecting an image of the site of interest by analyzing the base map, and a process of designating an area of interest based on the detected image of the site of interest. The automatic designation of another example includes a process of detecting an image of a site of interest by analyzing an image of the eye 120 acquired additionally, a process of identifying an area in the base map corresponding to the detected image in the image of the eye 120 by comparing the image of the eye 120 with the base map, and a process of designating an area of interest based on the area identified.

Some effects of the ophthalmic apparatus (OCT apparatus) 100 of the present aspect will be described.

The ophthalmic apparatus 100 of the present aspect includes the OCT scanner 220, the scan controlling unit 210 (the first controlling unit, the second controlling unit), the map creating unit 202, the region designating unit 204, and the image data generating unit 206. The OCT scanner 220 is configured to apply an OCT scan to a sample (the eye 120). The scan controlling unit 210 is configured to control the OCT scanner 200 to acquire the first three dimensional data set by applying an OCT scan targeting the first three dimensional region of the eye 120. The map creating unit 202 is configured to create the first two dimensional map based on representative intensity values respectively of a plurality of pieces of A-scan data included in the first three dimensional data set. The region designating unit 204 is configured to designate the second three dimensional region of the eye 120 based on the first two dimensional map. The scan controlling unit 210 is configured to control the OCT scanner 220 to acquire the second three dimensional data set by applying an OCT scan targeting the second three dimensional region. The image data generating unit 206 is configured to generate image data from at least part of the second three dimensional data set.

The ophthalmic apparatus 100 configured as described above is capable of constructing an image of at least part of the region designated based on the two dimensional map created from the three dimensional data set acquired by an OCT scan. Therefore, an image of a desired region can be acquired without having to perform the three dimensional image construction and/or the landmark detection (landmark identification) as in the invention described in U.S. Pat. Nos. 7,884,945 and 8,405,834. This leads to improvement in the efficiency of resources required for processing and to shortening of the processing time, and contributes to further improvement in the efficiency of OCT scanning and OCT data processing. Thereby, for example, real-time processing can be realized in an appropriate and suitable manner. Note that at least one of hardware and software may be separate, or both may be the common for the first and second controlling units.

In the ophthalmic apparatus 100 of the present aspect, the region designating unit 204 may be configured to, based on the first two dimensional map created by the map creating unit 202, designate a target region that is a three dimensional region included in the eye 120 (the first three dimensional region) corresponding to the first two dimensional map, and then designate the second three dimensional region to include the target region. Further, the region designating unit 204 may be configured to designate the second three dimensional region to include the target region and be included in the first three dimensional region.

According to the configuration described above, an image of a desired region (a target region) to be referred to in processing, tasks and operations such as diagnosis, analysis and evaluation can be acquired in an efficient and more reliable manner.

In the ophthalmic apparatus 100 of the present aspect, the map creating unit 202 may be configured to create the second two dimensional map based on representative intensity values respectively of a plurality of pieces of A-scan data included in the second three dimensional data set. In addition, the image data generating unit 206 may be configured to designate a partial data set of the second three dimensional data set by a comparison of the first and second two dimensional maps, and generate image data from the partial data set.

According to the configuration mentioned above, the partial data set to be used for imaging can be designated through the comparison of the two dimensional maps, without having to go through a process that requires many resources such as three dimensional image construction and comparison of three dimensional images obtained thereby.

In the ophthalmic apparatus 100 of the present aspect, the comparison between the first and second two dimensional maps may include the image correlation calculation. Furthermore, the positional difference amount between the first and second two dimensional maps may be determined by the comparison. The positional difference amount may include at least one of the translation amount and the rotation amount.

According to such a configuration, the relationship between the two dimensional maps can be obtained in an efficient manner by using image correlation (typically, phase only correlation) without having to involve processing that requires many resources such as landmark detection.

In the ophthalmic apparatus 100 of the present aspect, the region designating unit 204 may be configured to perform, based on the first two dimensional map, a process of designating a target region that is a three dimensional region included in the first three dimensional region, and a process of designating the second three dimensional region to include the target region and be included in the first three dimensional region. Further, the image data generating unit 206 may be configured to designate the partial data set by designating part of the second three dimensional data set corresponding to the target region, based on the result of the comparison between the first and second two dimensional maps.

According to the configuration described above, an image of a desired region (a target region) to be referred to in processing, tasks and operations such as diagnosis, analysis and evaluation can be acquired in an efficient and more reliable manner, with the comparison between the two dimensional maps, without having to go through a process that requires many resources such as three dimensional image construction and comparison of three dimensional images obtained thereby.

In the ophthalmic apparatus 100 of the present aspect, the image data generating unit 206 may be configured to determine whether or not the second three dimensional data set includes the target data set corresponding to the target region, based on the result of the comparison between the first and second two dimensional maps.

According to the configuration described above, without having to go through a process that requires many resources such as three dimensional image construction and comparison of three dimensional images obtained thereby, but with the comparison between the two dimensional maps, the determination can be carried out whether or not an image of a desired region (a target region) to be referred to in processing, tasks and operations such as diagnosis, analysis, and evaluation can be obtained from the second three dimensional data set.

In the ophthalmic apparatus 100 of the present aspect, the image data generating unit 206 may be configured to designate the target data set to be the partial data set to be used for imaging in the event that the second three dimensional data set is determined to include the target data set by the above determination based on the comparison of the two dimensional maps.

According to such a configuration, an image of the target region can be obtained from the target data set in the event that the second three dimensional data set includes the target data set. This makes it possible to obtain the target region image in an efficient and more reliable manner.

In the ophthalmic apparatus 100 of the present aspect, the scan controlling unit 210 may be configured to perform control of the OCT scanner to acquire a new second three dimensional data set by applying another OCT scan targeting the (previous, earlier, or new) second three dimensional region of the eye 120, in the event that the second three dimensional data is determined not to include the target data set by the above determination based on the comparison between the two dimensional maps. Further, the image data generating unit 206 may be configured to generate image data from at least part of the new second three dimensional data set.

According to such a configuration, another OCT scan may be applied to the eye 120 to obtain an image of the target region in the event that the second three dimensional data set is determined not to include the target data set. This makes it possible to obtain an image of the target region in an efficient and more reliable manner.

In the ophthalmic apparatus 100 of the present aspect, the region designating unit 204 may be configured to designate a new second three dimensional region of the eye 120 in the event that the second three dimensional data set is determined not to include the target data set. Further, the scan controlling unit 210 may be configured to perform control of the OCT scanner to acquire a new second three dimensional data set by applying an OCT scan targeting the new second three dimensional region. In addition, the image data generating unit 206 may be configured to generate image data from at least part of the new second three dimensional data set.

According to such a configuration, the second three dimensional region for obtaining an image of the target region can be newly designated and an OCT scan can be applied again to the eye 120, in the event that the second three dimensional data set is determined not to include the target data set. This makes it possible to obtain an image of the target region in an efficient and more reliable manner.

In the ophthalmic apparatus 100 of the present aspect, the region designating unit 204 may be configured to designate a new target region that is a three dimensional region included in the first three dimensional region, and designate a new second three dimensional region to include the new target region, in the event that the second three dimensional data set is determined not to include the target data set.

Here, the region designating unit 204 may be configured to designate the new second three dimensional region to include the new target region and be included in the first three dimensional region, in the event that the second three dimensional data set is determined not to include the target data set and then the new target region is designated. Further, the region designating unit 204 may be configured to designate the new second three dimensional region based on the result of the comparison between the first and second two dimensional maps. Furthermore, the region designating unit 204 may be configured to designate the new second three dimensional region by changing a position (location) of the second three dimensional region based on the result of the comparison. In addition, the size of the new second three dimensional region may be larger than that of the second three dimensional region applied previously (or earlier).

Further, the scan controlling unit 210 may be configured to perform control of the OCT scanner to acquire a new second three dimensional data set by applying an OCT scan targeting the new second three dimensional region. In addition, the image data generating unit 206 may be configured to generate image data from at least part of the new second three dimensional data set.

According to the configuration as described above, an image of the new target region may be obtained by newly designating the target region and the second three dimensional region and performing another OCT scan on the eye 120, in the event that the second three dimensional data set is determined not to include the target data set. This makes it possible to acquire an image of a desired region of the eye 120 in an efficient and more reliable manner.

As described above, although the sample of the present aspect is a living eye, the same or like functions and/or configurations may be applied to an OCT apparatus intended for a sample other than living eyes. More specifically, any of the items (functions, hardware configurations, software configurations, etc.) regarding the ophthalmic apparatus 100 may be combined with an OCT apparatus of any aspect. The items combined yield or provide corresponding actions and effects.

Some aspects relate to a method of controlling an OCT apparatus that includes a processor and an OCT scanner that applies an OCT scan to a sample. The controlling method may include at least the following steps: a step of controlling the OCT scanner to acquire the first three dimensional data set by applying an OCT scan targeting the first three dimensional region of a sample; a step of controlling the processor to create the first two dimensional map based on representative intensity values respectively of a plurality of pieces of A-scan data included in the first three dimensional data set; a step of controlling the processor to designate the second three dimensional region of the sample based on the first two dimensional map; a step of controlling the OCT scanner to acquire the second three dimensional data set by applying an OCT scan targeting the second three dimensional region; and a step of controlling the processor to generate image data from at least part of the second three dimensional data set.

Any of the items (functions, hardware configurations, software configurations, etc.) regarding the ophthalmic apparatus 100 may be combined with the controlling method of the present aspect. The items combined yield or provide corresponding actions and effects.

Some aspects relate to a program that causes a computer to execute the method of controlling an OCT apparatus. Any of the items described for the ophthalmic apparatus 100 may be combined with the program. Further, some aspects relate to a computer-readable non-transitory recording medium storing such a program. Any of the items described for the ophthalmic apparatus 100 may be combined with the recording medium.

Some aspects relate to an apparatus for processing data acquired using OCT (referred to as an OCT data processing apparatus). The OCT data processing apparatus may include at least the following elements: the first receiving unit configured to receive the first three dimensional data set acquired by an OCT scan targeting the first three dimensional region of a sample; a map creating unit configured to create the first two dimensional map based on representative intensity values respectively of a plurality of pieces of A-scan data included in the first three dimensional data set; a region designating unit configured to designate the second three dimensional region of the sample based on the first two dimensional map; the second receiving unit configured to receive the second three dimensional data set acquired by an OCT scan targeting the second three dimensional region; and an image data generating unit configured to generate image data from at least part of the second three dimensional data set.

It may also be said that the OCT data processing apparatus includes elements (the first receiving unit, the second receiving unit) that receive three dimensional data sets obtained by OCT scanning from an external device (e.g., OCT apparatus, image archiving system, recording medium), instead of (or in addition to) the OCT scanner 220 of the above-described OCT apparatus (ophthalmic apparatus) 100. Regarding the first and second receiving units, at least one of the hardware and the software may be separate, or both may be the common. The first receiving unit (the second receiving unit) may include, for example, a communication device or a drive device.

Any of the items (functions, hardware configurations, software configurations, etc.) regarding the ophthalmic apparatus 100 may be combined with the OCT data processing apparatus of the present aspect. The items combined yield or provide corresponding actions and effects.

Some aspects relate to a method of controlling an OCT data processing apparatus that includes a processor. The controlling method may include at least the following steps: a step of controlling the processor to receive the first three dimensional data set acquired by an OCT scan targeting the first three dimensional region of a sample; a step of controlling the processor to create the first two dimensional map based on representative intensity values respectively of a plurality of pieces of A-scan data included in the first three dimensional data set; a step of controlling the processor to designate the second three dimensional region of the sample based on the first two dimensional map; a step of controlling the processor to receive the second three dimensional data set acquired by an OCT scan targeting the second three dimensional region; and a step of controlling the processor to generate image data from at least part of the second three dimensional data set.

Any of the items (functions, hardware configurations, software configurations, etc.) regarding the ophthalmic apparatus 100 may be combined with the controlling method of the present aspect. The items combined yield or provide corresponding actions and effects.

Some aspects relate to a program that causes a computer to execute such a method of controlling an OCT data processing apparatus. With this program, it is possible to combine any of the items described for the ophthalmic apparatus 100. Further, some aspects relate to a computer-readable non-transitory recording medium storing such a program. Any of the items described for the ophthalmic apparatus 100 may be combined with the recording medium.

Any of an OCT apparatus (e.g., the ophthalmic apparatus 100) of some aspects, a controlling method of an OCT apparatus of some aspects, an OCT data processing apparatus of some aspects, and a controlling method of an OCT data processing apparatus of some aspects provides a method of OCT imaging. The OCT imaging method may include at least the following steps: a step of acquiring the first three dimensional data set by applying an OCT scan targeting the first three dimensional region of a sample; a step of creating the first two dimensional map based on representative intensity values respectively of a plurality of pieces of A-scan data included in the first three dimensional data set; a step of designating the second three dimensional region of the sample based on the first two dimensional map; a step of acquiring the second three dimensional data set by applying an OCT scan targeting the second three dimensional region; and a step of generating image data from at least part of the second three dimensional data set.

Any of the items (functions, hardware configurations, software configurations, etc.) regarding the ophthalmic apparatus 100 may be combined with the OCT imaging method of the present aspect. The items combined yield or provide corresponding actions and effects.

Some aspects relate to a program that causes a computer to execute such an OCT imaging method. With this program, it is possible to combine any of the items described for the ophthalmic apparatus 100. Further, some aspects relate to a computer-readable non-transitory recording medium storing such a program. Any of the items described for the ophthalmic apparatus 100 may be combined with the recording medium.

Some aspects provide a method of processing data acquired using OCT. The OCT data processing method may include at least the following steps: a step of receiving the first three dimensional data set acquired by an OCT scan targeting the first three dimensional region of a sample; a step of creating the first two dimensional map based on representative intensity values respectively of a plurality of pieces of A-scan data included in the first three dimensional data set; a step of designating the second three dimensional region of the sample based on the first two dimensional map; a step of receiving the second three dimensional data set acquired by an OCT scan targeting the second three dimensional region; and a step of generating image data from at least part of the second three dimensional data set.

Any of the items (functions, hardware configurations, software configurations, etc.) regarding the ophthalmic apparatus 100 may be combined with the OCT data processing method of the present aspect. The items combined yield or provide corresponding actions and effects.

Some aspects relate to a program that causes a computer to execute such an OCT data processing method. With this program, it is possible to combine any of the items described for the ophthalmic apparatus 100. Further, some aspects relate to a computer-readable non-transitory recording medium storing such a program. Any of the items described for the ophthalmic apparatus 100 may be combined with the recording medium.

The non-transitory recording medium may be in any form, and examples thereof include a magnetic disk, optical disk, magneto-optical disk, semiconductor memory, and the like.

While certain embodiments have been described, these embodiments have been presented by way of example only, and are not intended to limit the scope of the inventions. Indeed, the novel embodiments described herein may be embodied in a variety of other forms; furthermore, various omissions, substitutions, additions and changes in the form of the embodiments described herein may be made without departing from the spirit of the inventions. The accompanying claims and their equivalents are intended to cover such forms or modifications as would fall within the scope and spirit of the inventions.

What is claimed is:

1. A method of imaging using optical coherence tomography (OCT), comprising:
   acquiring a first three dimensional data set by applying an OCT scan targeting a first three dimensional region of a sample;
   creating a first two dimensional map based on representative intensity values respectively of a plurality of pieces of A-scan data included in the first three dimensional data set;
   designating a second three dimensional region of the sample based on the first two dimensional map;
   acquiring a second three dimensional data set by applying an OCT scan targeting the second three dimensional region; and
   generating image data from at least part of the second three dimensional data set,
   wherein the designating the second three dimensional region includes
      analyzing the first two dimensional map to detect an image of a predetermined site of the sample, and
      designating the second three dimensional region in such a way that the image detected is placed in a predetermined position within the second three dimensional region.

2. The OCT imaging method of claim 1, wherein designating the second three dimensional region includes: based on the first two dimensional map,
   designating a target region that is a three dimensional region included in the first three dimensional region; and
   designating the second three dimensional region to include the target region.

3. The OCT imaging method of claim 2, wherein designating the second three dimensional region to include the target region and be included in the first three dimensional region.

4. The OCT imaging method of claim 1, wherein generating the image data includes:
   creating a second two dimensional map based on representative intensity values respectively of a plurality of pieces of A-scan data included in the second three dimensional data set;
   designating a partial data set of the second three dimensional data set by a comparison between the first two dimensional map and the second two dimensional map; and
   generating the image data from the partial data set.

5. The OCT imaging method of claim 4, wherein the comparison includes an image correlation calculation.

6. The OCT imaging method of claim 4, further comprising determining a positional difference amount between the first two dimensional map and the second two dimensional map by the comparison.

7. The OCT imaging method of claim 6, wherein the positional difference amount includes at least one of a translation amount and a rotation amount.

8. The OCT imaging method of claim 4, wherein designating the second three dimensional region includes: based on the first two dimensional map,
   designating a target region that is a three dimensional region included in the first three dimensional region; and
   designating the second three dimensional region to include the target region and be included in the first three dimensional region, and
   designating the partial data set by designating part of the second three dimensional data set corresponding to the target region based on a result of the comparison.

9. The OCT imaging method of claim 8, further comprising determining whether or not the second three dimensional data set includes a target data set corresponding to the target region based on the result of the comparison.

10. The OCT imaging method of claim 9, wherein designating the target data set as the partial data set in the event that the second three dimensional data set is determined to include the target data set.

11. The OCT imaging method of claim 9, further comprising:
   acquiring another second three dimensional data set by applying another OCT scan targeting the second three dimensional region of the sample in the event that the second three dimensional data is determined not to include the target data set; and
   generating image data from at least part of the another second three dimensional data set.

12. The OCT imaging method of claim 11, further comprising designating another second three dimensional region of the sample in the event that the second three dimensional data set is determined not to include the target data set, wherein
   acquiring the another second three dimensional data set by applying an OCT scan targeting the another second three dimensional region.

13. The OCT imaging method of claim 12, wherein designating the another second three dimensional region includes:
   designating another target region that is a three dimensional region included in the first three dimensional region; and
   designating the another second three dimensional region to include the another region.

14. The OCT imaging method of claim 13, wherein designating the another second three dimensional region to include the another target region and be included in the first three dimensional region.

15. The OCT imaging method of claim 12, wherein designating the another second three dimensional region based on the result of the comparison.

16. The OCT imaging method of claim 15, wherein designating the another second three dimensional region by changing a position of the second three dimensional region based on the result of the comparison.

17. The OCT imaging method of claim 12, wherein a size of the another second three dimensional region is larger than a size of the second three dimensional region.

18. A method of processing data acquired using optical coherence tomography (OCT), comprising:
   receiving a first three dimensional data set acquired by applying an OCT scan targeting a first three dimensional region of a sample;
   creating a first two dimensional map based on representative intensity values respectively of a plurality of pieces of A-scan data included in the first three dimensional data set;
   designating a second three dimensional region of the sample based on the first two dimensional map;
   receiving a second three dimensional data set acquired by an OCT scan targeting the second three dimensional region; and
   generating image data from at least part of the second three dimensional data set,
   wherein the designating the second three dimensional region includes
      analyzing the first two dimensional map to detect an image of a predetermined site of the sample, and
      designating the second three dimensional region in such a way that the image detected is placed in a predetermined position within the second three dimensional region.

19. An optical coherence tomography (OCT) apparatus comprising:
   an OCT scanner that applies an OCT scan to a sample;
   first controlling circuitry that controls the OCT scanner to acquire a first three dimensional data set by applying an OCT scan targeting a first three dimensional region of a sample;
   map creating circuitry that creates a first two dimensional map based on representative intensity values respectively of a plurality of pieces of A-scan data included in the first three dimensional data set;
   region designating circuitry that designates a second three dimensional region of the sample based on the first two dimensional map;
   second controlling circuitry that controls the OCT scanner to acquire a second three dimensional data set by applying an OCT scan targeting the second three dimensional region; and
   image data generating circuitry that generates image data from at least part of the second three dimensional data set,
   wherein the region designating circuit is further configured to
      analyze the first two dimensional map to detect an image of a predetermined site of the sample, and,
      designate the second three dimensional region in such a way that the image detected is placed in a predetermined position within the second three dimensional region.

* * * * *